United States Patent
Harton et al.

(10) Patent No.: US 9,163,071 B2
(45) Date of Patent: Oct. 20, 2015

(54) POP2: NKκB-INHIBITING POLYPEPTIDES, NUCLEIC ACIDS AND METHODS OF USE

(75) Inventors: Jonathan A. Harton, Tampa, FL (US); Felipe Bedoya, Tampa, FL (US); Laurel L. Sandler, Tampa, FL (US)

(73) Assignee: University of South Florida, Tampa, FL (US)

( * ) Notice: Subject to any disclaimer, the term of this patent is extended or adjusted under 35 U.S.C. 154(b) by 1329 days.

(21) Appl. No.: 11/279,043

(22) Filed: Apr. 7, 2006

(65) Prior Publication Data

US 2007/0031410 A1    Feb. 8, 2007

Related U.S. Application Data

(60) Provisional application No. 60/669,283, filed on Apr. 7, 2005.

(51) Int. Cl.
| | |
|---|---|
| C12N 15/63 | (2006.01) |
| C12N 15/12 | (2006.01) |
| A61K 31/711 | (2006.01) |
| C07K 14/47 | (2006.01) |
| G01N 33/68 | (2006.01) |
| A61K 38/00 | (2006.01) |

(52) U.S. Cl.
CPC ........ C07K 14/4703 (2013.01); G01N 33/6872 (2013.01); A61K 38/00 (2013.01); G01N 2500/00 (2013.01)

(58) Field of Classification Search
CPC ................................ C12N 15/52; C12N 15/11
See application file for complete search history.

(56) References Cited

U.S. PATENT DOCUMENTS

| | | | |
|---|---|---|---|
| 2003/0017983 A1 | 1/2003 | Bertin et al. | |
| 2004/0053292 A1* | 3/2004 | Tschopp et al. | .......... 435/6 |
| 2004/0072228 A1 | 4/2004 | Glynne et al. | |

OTHER PUBLICATIONS

Richard, Protein stability: still an unsolved problem (1997) Cell Mol. Life Sci. 53:790-802.*
AY858112, Apr. 1, 2005, Homo sapiens pyrin-only protein 2 (POP2) mRNA, complete cds.*
Gumucio et al, Clinical and Experimental Rheumatology, 2002, vol. 20 (pp. S45-S53).*
Guo et al, Protein tolerance to random amino acid change, PNAS, 2004, vol. 101 (25), pp. 9205-9210.*
Lesk et al, Prediction of Protein Function from Protein Sequence and Structure, p. 27 and 28, downloaded Sep. 16, 2007.*
Bedoya et al, Pyrin-Only Protein 2 Modulates NF-kB and Disrupts ASCCLR Interactions, J Immun.1., Mar. 15, 2007 vol. 178 No. 6 3837-3845.*
Reirs et al, Production of tumor necrosis factor-alpha and interferon-gamma from human peripheral blood lymphocytes by MGN-3, a modified arabinoxylan from rice bran, and its synergy with interleukin-2 in vitro, Toxicological Science, 2001, vol. 60, pp. 327-337.*
Baker, D. 2000. "A Surprising Simplicity to Protein Folding." Nature. vol. 405. pp. 39-42.

* cited by examiner

*Primary Examiner* — Maria Marvich
(74) *Attorney, Agent, or Firm* — Michele L. Lawson; Michael M. McGaw; Smith & Hopen, P.A.

(57) ABSTRACT

This invention provides a novel pyrin-only protein (POP2), polypeptides, and nucleic acids encoding them and methods for making and using them. POP2 is a 294 nt single exon gene located on human chromosome 3 encoding a 97 amino acid protein with sequence and predicted structural similarity to other pyrin domains. Highly similar to pyrin domains in CATERPILLER (CLR, NLR, NALP) family proteins, POP2 is less like the prototypic Pyrin and ASC pyrin domains. POP2 is expressed principally in peripheral blood leukocytes and displays both cytoplasmic and nuclear expression patterns in transfected cells. TNFα-stimulated and p65 (RelA) induced NF-κB-dependent gene transcription is inhibited by POP2 in vitro by a mechanism involving changes in NF-κB nuclear import or distribution. While colocalizing with ASC in perinuclear specks, POP2 also inhibits the formation of specks by the CLR protein CIAS1/NALP3. POP2 is a negative regulator of NF-κB activity that may influence the assembly of pyrin-domain dependent complexes.

1 Claim, 12 Drawing Sheets

FIG. 3

```
        M   A   S   S   A   E   L   D   F   N   L   Q   A   L   L   E   Q   L   S   Q  20
  1   ATG GCA TCT TCT GCA GAG CTG GAC TTC AAC CTG CAG GCT CTT CTG GAG CAG CTC AGC CAG
        D   E   L   S   K   F   K   S   L   I   R   T   I   S   L   G   K   E   L   Q  40
 61   GAT GAG TTG AGC AAG TTC AAG TCT CTG ATC AGA ACA ATC TCC CTG GGA AAG GAG CTA CAG
        T   V   P   Q   T   E   V   D   K   A   N   G   K   Q   L   V   E   I   F   T  60
121   ACC GTC CCC CAG ACA GAG GTA GAC AAG GCT AAT GGG AAG CAA CTG GTA GAA ATC TTC ACC
        S   H   S   C   S   Y   W   A   G   M   A   A   I   Q   V   F   E   K   M   N  80
181   AGC CAC TCC TGC AGC TAC TGG GCA GGG ATG GCA GCC ATC CAG GTC TTT GAA AAG ATG AAT
        Q   T   H   L   S   G   R   A   D   E   H   C   V   M   P   P   P   *  3' UTR  97
241   CAA ACG CAT CTG TCT GGG AGA GCT GAT GAA CAC TGT GTG ATG CCC CCA CCT TAA CCCCTCA

302   GGGATAGTGAGTTGATGGCTGAGCTAGATGTTGCTTTAGCCTTGGTTCTGTCTCCATTTTACATGCACATGTTGCTTAA
                                                                                  polyA
381   CCTTGTTATATATGAAATATCTATATCACCAGTATTTTGAGATAAATAAAGGTGAAATAATTCACAAACATTAAAA(A)ₙ
```

FIG. 4

FIG. 11
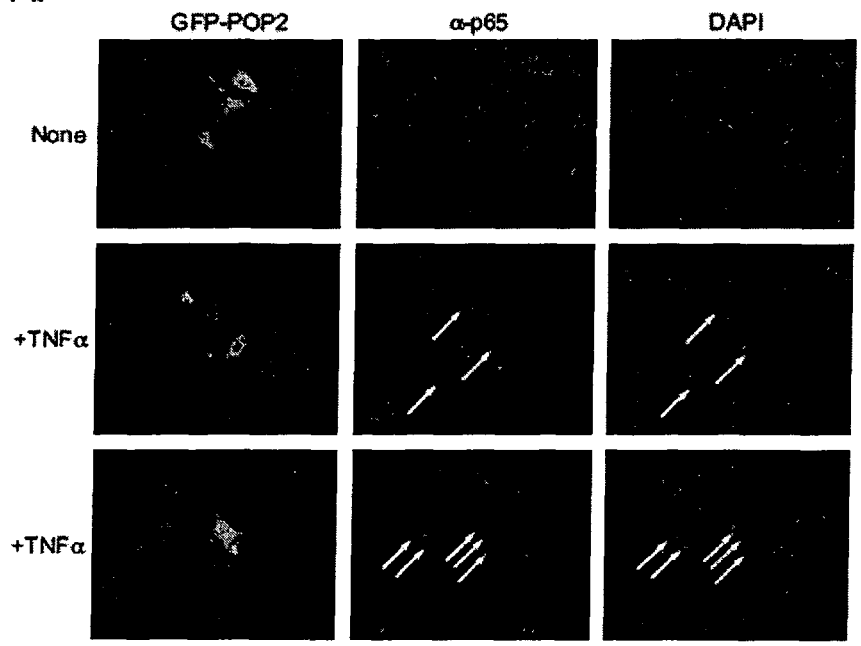
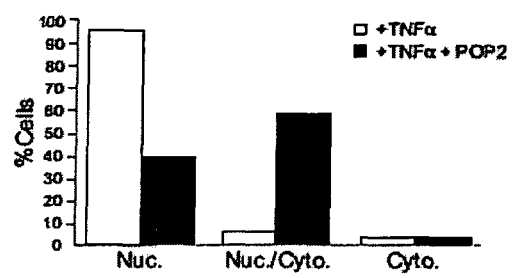

POP2: NKκB-INHIBITING POLYPEPTIDES, NUCLEIC ACIDS AND METHODS OF USE

CROSS REFERENCE TO RELATED APLICATIONS

This application claims priority to currently pending U.S. Provisional Patent Application 60/669,283, entitled, "POP2: A Biological Inhibitor of NF Kappa B", filed Apr. 7, 2005.

FIELD OF INVENTION

This invention relates to regulators of biological processes including cell growth, cell death and the production of cytokines. More particularly, this invention relates to a novel Pyrin-only Protein (POP2) having an inhibitory effect on NF-κB.

BACKGROUND OF INVENTION

Activation of NF-κB regulates numerous cellular processes including cytokine and adhesion molecule expression, cell-cycle regulation and cell growth. Constitutive or excessive NF-κB activity is thus observed in inflammatory diseases, autoimmunity and cancer. Notably, active NF-κB also protects against apoptosis which may contribute to the accumulation of inflammatory, self-reactive or cancerous cells.

Extensive research has been conducted throughout the last decade towards understanding the molecular mechanism, signaling pathways and physiological role of proteins containing the death domain fold (DDF) associated with NF-κB signaling and apoptosis induction. Four related protein-protein interaction domains comprise the DDF superfamily: the death domain (DD); the death effector domain (DED); the caspase recruitment domain (CARD) and the pyrin domain (PYD). These domains share a similar tertiary structure, a 5 to 6 α-helical bundle that likely function as homotypic interaction modules. Acting as signaling adapters and recruiters of proteins into sub-cellular complexes domains of this type participate in the promotion and regulation of apoptosis, innate immunity and cancer development.

Pyrin motifs are generally found at the N-terminus of multidomain proteins. Pyrin (marenostrin), the founding member of the family, is associated with Familial Mediterranean Fever (FMF), an autosomal recessive disease characterized by sporadic attacks of fever and intense abdominal, joint and chest pain. Following its PYD, Pyrin contains a B-box zinc finger and a SPRY domain believed to function as adaptor and ligand binding units, respectively. Interferon inducible (IFI) genes, which code for the HIN-200 family of hematopoetic nuclear proteins and contain one or two copies of a 200-amino-acid domain believed to mediate protein/protein interactions, are preceded by a PYD. Evidence supporting the role of HIN-200 proteins in controlling cell proliferation and differentiation has been previously documented. The pyrin domain of Apoptosis speck protein containing a CARD, ASC (TMS1/Pycard) is followed by a CARD domain. ASC associates with PYD- or CARD-containing proteins through homotypic interactions via both domains. In proapoptotic cells, ASC assembles in large multimeric perinuclear complexes or 'specks' by interacting with PYD-containing proteins. The physiological significance of these interactions and that of the speck structure itself remains unclear. ASC also participates in the formation of the inflammasome complex that processes pro IL-1β into the mature form and is up-regulated in neutrophils during inflammation. Two thirds of the 21 members of the recently discovered CATERPILLER (CLR) gene family thought to play an important role in vertebrate immunity functioning as intracellular pathogen-recognizing units, encode a PYD followed by a nucleotide binding domain (NBD) and leucine-rich repeats domain (LRR). CLR proteins have been postulated as modulators of ongoing inflammatory responses and as inducers of apoptosis. Some PYD-containing proteins of the CLR family have been reported to induce NF-κB activation in conjunction with ASC, including PYPAF5, Monarch, and CIAS1. Not surprisingly, mutations in CIAS1/NALP3 associated with the inflammatory syndromes familial cold urticaria, Muckle-Wells, and chronic infantile neurologic cutaneous articular syndrome, showed increased capacity for ASC-dependent NF-κB activation. Other CLRs, such as PAN2/PYPAF4 mediate NF-κB suppression. Although the NBD/LRR of CIAS1 inhibits NF-κB nuclear import, the pyrin domain of PAN2/PYPAF4 inhibits NF-κB, a function that may be mediated through the IKK complex.

The NF-κB family of transcription factors is comprised of five members in mammals: p65 (Rel A), Rel B, c-Rel, p50/p105 and p52/p100, existing as homo- or heterodimers bound to the IκB inhibitory complex in the cytosol. Upon induction by proinflammatory stimuli such as TNF-α or LPS, IκBα is phosphorylated by the IκB kinase (IKK) complex, ubiquitinated and degraded by the 26S proteasome. This process unmasks NF-κB's nuclear localization sequence, leading to its translocation into the nucleus. Binding of NF-κB to its cognate DNA response elements induces the transcription of a host of cytokines and growth factors (e.g. IL-2, Il-8, IFN-β, M-CSF, G-CSF, VEGF), as well as various transcription factors and signaling regulators (e.g. IκBα, IRF-1, IRF-2). The pivotal role of NF-κB in biological processes modulating the immune response suggests that localization and subsequent activation must be rigorously controlled. Dysregulation of these events leads to aberrant gene expression associated with numerous human diseases including cancer, neurodegenerative disorders, arthritis and chronic inflammation.

Solitary pyrin domains may disrupt pyrin domain interactions, potentially blocking the formation of speck and/or inflammasome complexes and their downstream effects. Genes comprised exclusively of a PYD have recently been identified in the human genome and in the genomes of pox viruses. Pyrin-only protein 1 (POP1), is encoded by a gene in the close proximity to ASC, suggesting that Pop1 might have arisen from an ancient gene duplication event. POP1 is predominantly expressed in immune tissues where it appears to inhibit NF-κB- and surprisingly enhances caspase-1-activation. Other genes encoding Pyrin-only proteins have been found in the genomes of Capripoxviridae, Leporipoxviridae, Suipoxviridae, and Yatapoxviridae. Recently, Johnston et al. reported that M13L-PYD (a Pyrin-only protein) from myxoma virus inhibits both NF-κB activity and Caspase-1-dependent IL-1b production and M13L deletion was sufficient to inhibit virus replication in vivo. (Johnston, J. B., et al. A poxvirus-encoded pyrin domain protein interacts with ASC-1 to inhibit host inflammatory and apoptotic responses to infection. *Immunity* 23:587). Therefore, PYDs have an active role as suppressors of host immunity. Modulating NF-κB signaling pathways is one potential mechanism for such suppression.

The completion of the human genome and the sequencing of the genomes of other species have resulted in the emergence of novel genes and the identification of new gene families. The recently described CLR family encompasses PYD-proteins with roles in both innate and acquired immunity.

Because of our interest in this gene family, we sought to identify new PYD-encoding genes.

SUMMARY OF INVENTION

A novel human Pyrin-only protein comprised of 97 amino acids that has been named POP2 is described. POP2 is encoded by a single exon gene on chromosome 3 and expressed in peripheral blood leukocytes. We demonstrate that POP2 inhibits NF-κB (RelA) activated by TNFa or transfection of p65 involving a subcellular redistribution of p65 NF-κB. In addition, POP2 associates with ASC in perinuclear speck structures, but inhibits specks composed of CIAS1/NALP3 and ASC. Collectively, these results imply an important role for POP2 as a negative regulator of the NF-κB signaling pathway and suggest a regulatory mechanism for CIAS1-dependent inflammatory responses.

The present invention provides Pyrin-only protein (POP2), polypeptides, nucleic acids encoding them and methods for making and using them. In one aspect, the polypeptides of the invention have NFκB inhibiting activity. The invention also provides pharmaceutical compositions comprising a nucleic acid or polypeptide of the invention.

In one aspect, the invention provides an isolated or recombinant nucleic acid comprising a nucleic acid sequence having at least 90% sequence identity to SEQ ID NO:1, wherein the nucleic acid encodes at least one polypeptide having an NFκB inhibiting activity.

The invention provides isolated or recombinant nucleic acids comprising a nucleic acid sequence having at least 90% sequence identity to SEQ ID NO:1 over a region of at least about 50 residues, wherein the nucleic acids encode at least one polypeptide having an NFκB inhibiting activity. The sequence identities can be determined by analysis with a sequence comparison algorithm or by a visual inspection.

In alternative aspects, the isolated or recombinant nucleic acids comprise a nucleic acid sequence having at least 90%, 91%, 92%, 93%, 94%, 95%, 96%, 97%, 98%, 99% or more sequence identity to SEQ ID NO:1 over a region of at least about 50, 60, 70, 80, 90, 100, 120, 140, 160, 180, 200, 220, 240, 260, 280, 300 or more residues. In one aspect, the isolated or recombinant nucleic acid has a sequence as set forth in SEQ ID NO:1.

In another aspect, the invention provides first nucleic acid molecule for identifying a second nucleic acid molecule, wherein the second nucleic acid molecule encodes a polypeptide with an NFκB inhibiting activity, wherein the first nucleic acid molecule comprises at least 10 consecutive bases of a sequence as set forth in SEQ ID NO:1, and further wherein the first nucleic acid molecule identifies the second nucleic acid molecule by binding or hybridization.

The invention provides nucleic acid probes for identifying a nucleic acid encoding a polypeptide with an NFκB inhibiting activity or a POP2 gene or variant thereof, wherein the probe comprises at least 10 consecutive bases of a sequence as set forth in SEQ ID NO:1 wherein the probe identifies the nucleic acid by binding or hybridization. The probe preferably comprises at least 15, 16, 17, 18, 19, 20, 21, 22, 23, 24 or 25 consecutive bases. The invention provides nucleic acid probes for identifying a nucleic acid encoding a polypeptide with an NFκB inhibiting activity or a POP2 gene or variant thereof, wherein the probe comprises a nucleic acid sequence having at least 90%, 91%, 92%, 93%, 94%, 95%, 96%, 97%, 98%, 99% or more sequence identity to SEQ ID NO:1 over a region of at least about 50, 60, 70, 80, 90, 100, 120, 140, 160, 180, 200, 220, 240, 260, 280, 300 or more residues. The sequence identities can be determined by analysis with a sequence comparison algorithm or by visual inspection. In alternative aspects, the probe comprises an oligonucleotide comprising at least about 10 to 50, about 20 to 60, about 30 to 70, about 40 to 80, or about 60 to 100 consecutive bases of a sequence as set forth in SEQ ID NO:1. The probe preferably comprises at least 15, 16, 17, 18, 19, 20, 21, 22, 23, 24 or 25 consecutive bases. In alternative aspects, the probe is about 30, 40, 50, 60, 70, 80, 90, 100, 110, 120, 130, 140, 150, 200, 250, 300, or more residues in length. In one aspect, the probe comprises a subset of a sequence as set forth in SEQ ID NO:1.

The invention provides an amplification primer sequence pair for amplifying a nucleic acid of the invention, e.g., a nucleic acid encoding a polypeptide with an NFκB inhibiting activity. The primer pair can be capable of amplifying a nucleic acid sequence as set forth in SEQ ID NO:1. In one aspect, each member of the amplification primer sequence pair comprises an oligonucleotide comprising at least about 10 to 50 consecutive bases of the sequence.

The invention provides methods of amplifying a nucleic acid encoding a polypeptide with an NFκB inhibiting activity or a POP2 gene or variant thereof, comprising amplification of a template nucleic acid with an amplification primer sequence pair capable of amplifying a nucleic acid sequence as set forth in SEQ ID NO:1.

In further aspects, the invention provides an expression cassette, a vector, or a transformed cell comprising a nucleic acid comprising a nucleic acid sequence having at least 90% sequence identity to SEQ ID NO:1. The transformed cell may be a bacterial cell, a mammalian cell, a fungal cell, a yeast cell, an insect cell or a plant cell. The invention further provides a cloning vehicle comprising a nucleic acid sequence having at least 90% sequence identity to SEQ ID NO:1. The nucleic acid sequence may be contained within a recombinant virus, a plasmid, a phage, a phagemid, a cosmid, a fosmid, a bacteriophage or an artificial chromosome.

The invention provides expression cassettes comprising a nucleic acid of the invention, e.g., a nucleic acid sequence having at least 90% sequence identity to SEQ ID NO:1 over a region of at least about 100 residues, wherein the sequence identities are determined by analysis with a sequence comparison algorithm or by visual inspection, or, a nucleic acid that hybridizes under stringent conditions to a nucleic acid sequence as set forth in SEQ ID NO:1, or a subsequence thereof, or the complement of any thereof.

The invention provides vectors comprising a nucleic acid of the invention, e.g., a nucleic acid comprising a nucleic acid sequence having at least 90% sequence identity to SEQ ID NO:1 over a region of at least about 100 residues, wherein the sequence identities are determined by analysis with a sequence comparison algorithm or by visual inspection, or, a nucleic acid that hybridizes under stringent conditions to a nucleic acid sequence as set forth in SEQ ID NO:1, or a subsequence thereof, or the complement of any thereof.

The invention provides vector systems comprising a nucleic acid of the invention, e.g., a nucleic acid having at least 90% sequence identity to SEQ ID NO:1 over a region of at least about 100 residues, wherein the sequence identities are determined by analysis with a sequence comparison algorithm or by visual inspection, or, a nucleic acid that hybridizes under stringent conditions to a nucleic acid sequence as set forth in SEQ ID NO:1, or a subsequence thereof, or the complement of any thereof, operably linked to transcriptional control elements such that double stranded RNA molecules are produced, wherein the double stranded RNA molecules are complementary to or capable of hybridizing under stringent conditions to a nucleic acid sequence at least 90% sequence identity to SEQ ID NO:1 over a region of at least about 100 residues, wherein the sequence identities are determined by analysis with a sequence comparison algorithm or by visual inspection, or, a nucleic acid that hybridizes under stringent conditions to a nucleic acid sequence as set forth in SEQ ID NO:1, or a subsequence thereof, or the complement of any thereof. In one aspect, the vector systems and transcriptional control elements can generate intracellular double stranded RNA molecules.

The invention provides cloning vehicles comprising a nucleic acid of the invention, e.g., a nucleic acid sequence having at least 90% sequence identity to SEQ ID NO:1 over a region of at least about 100 residues, wherein the sequence identities are determined by analysis with a sequence comparison algorithm or by visual inspection, or, a nucleic acid that hybridizes under stringent conditions to a nucleic acid sequence as set forth in SEQ ID NO:1, or a subsequence thereof, or the complement of any thereof. In one aspect, the cloning vehicle comprises a recombinant virus, a plasmid, a phage, a phagemid, a cosmid, a fosmid, a bacteriophage or an artificial chromosome. The virus can comprise an adenovirus vector, a retroviral vector or an adeno-associated viral vector. The cloning vehicle can comprise a bacterial artificial chromosome (BAC), a plasmid, a bacteriophage P1-derived vector (PAC), a yeast artificial chromosome (YAC), a mammalian artificial chromosome (MAC).

The invention provides transformed cells comprising a vector, wherein the vector comprises a nucleic acid of the invention, e.g., a nucleic acid sequence having at least 90% sequence identity to SEQ ID NO:1 over a region of at least about 100 residues, wherein the sequence identities are determined by analysis with a sequence comparison algorithm or by visual inspection, or, a nucleic acid that hybridizes under stringent conditions to a nucleic acid sequence as set forth in SEQ ID NO:1, or a subsequence thereof, or the complement of any thereof. In alternative aspects, the cell is a bacterial cell, a mammalian cell, a fungal cell, a yeast cell, an insect cell or a plant cell.

In further aspects, the invention provides an antisense oligonucleotide comprising a nucleic acid sequence complementary to or capable of hybridizing under stringent conditions to a nucleic acid sequence with at least 90% sequence identity to SEQ ID NO:1; and a method of inhibiting an NFκB activity in a cell with this antisense oligonucleotide.

The invention provides antisense oligonucleotides comprising a nucleic acid of the invention, e.g., a nucleic acid sequence complementary to or capable of hybridizing under stringent conditions to a nucleic acid sequence at least 90% sequence identity to SEQ ID NO:1 over a region of at least about 100 residues, wherein the sequence identities are determined by analysis with a sequence comparison algorithm or by visual inspection, or, a nucleic acid that hybridizes under stringent conditions to a nucleic acid sequence as set forth in SEQ ID NO:1, or a subsequence thereof, or the complement of any thereof. The antisense oligonucleotide can be between about 10 to 50, about 20 to 60, about 30 to 70, about 40 to 80, or about 60 to 100 bases in length.

The invention provides methods of inhibiting an NFκB activity in a cell comprising administering to the cell or expressing in the cell an antisense oligonucleotide comprising a nucleic acid of the invention, e.g., a nucleic acid sequence complementary to or capable of hybridizing under stringent conditions to a nucleic acid sequence at least 90% sequence identity to SEQ ID NO:1 over a region of at least about 100 residues, wherein the sequence identities are determined by analysis with a sequence comparison algorithm or by visual inspection, or, a nucleic acid that hybridizes under stringent conditions to a nucleic acid sequence as set forth in SEQ ID NO:1, or a subsequence thereof, or the complement of any thereof.

In further aspects, the invention provides a double stranded RNA oligonucleotide comprising a nucleic acid sequence complementary to or capable of hybridizing under stringent conditions to a nucleic acid sequence with at least 90% sequence identity to SEQ ID NO:1. The invention further provides a method of inducing the degradation by RNA interference of a message in a cell comprising administering to the cell or expressing in the cell a double stranded RNA molecule, or a molecule predicted to fold into a double stranded form, or two complementary RNA molecules that are capable of hybridizing to form a double stranded RNA molecule, wherein the double stranded RNA molecule comprises a nucleic acid sequence complementary to or capable of hybridizing under stringent conditions to a nucleic acid sequence at least 90% sequence identity to SEQ ID NO:1.

The invention provides double stranded RNA oligonucleotides comprising a nucleic acid of the invention, e.g., a nucleic acid sequence complementary to or capable of hybridizing under stringent conditions to a nucleic acid sequence at least 90% sequence identity to SEQ ID NO:1 over a region of at least about 100 residues, wherein the sequence identities are determined by analysis with a sequence comparison algorithm or by visual inspection, or, a nucleic acid that hybridizes under stringent conditions to a nucleic acid sequence as set forth in SEQ ID NO:1, or a subsequence thereof, or the complement of any thereof. The double stranded RNA oligonucleotide can be between about 10 to 50, about 20 to 60, about 30 to 70, about 40 to 80, or about 60 to 100 bases in length.

The invention provides methods of inducing the degradation by RNA interference of a message in a cell comprising administering to the cell or expressing in the cell a double stranded RNA molecule, or a molecule predicted to fold into a double stranded form, or two complementary RNA molecules that are capable of hybridizing to form a double stranded RNA molecule, wherein the double stranded RNA molecule comprises a nucleic acid of the invention, e.g., a nucleic acid sequence complementary to or capable of hybridizing under stringent conditions to a nucleic acid sequence at least 90% sequence identity to SEQ ID NO:1 over a region of at least about 100 residues, wherein the sequence identities are determined by analysis with a sequence comparison algorithm or by visual inspection, or, a nucleic acid that hybridizes under stringent conditions to a nucleic acid sequence as set forth in SEQ ID NO:1, or a subsequence or complement thereof.

In another aspect, the invention provides an isolated or recombinant polypeptide comprising (i) an amino acid sequence having at least 95% sequence identity to SEQ ID NO:2; or (ii) an amino acid sequence encoded by a nucleic acid comprising a sequence having at least 90% sequence identity to SEQ ID NO:1; wherein the polypeptide has an NFκB inhibiting activity.

The invention provides isolated or recombinant polypeptides comprising an amino acid sequence having at least 95%, 96%, 97%, 98%, 99% or more sequence identity to SEQ ID NO:2 over a region of at least about 30, 40, 50, 60, 70, 80, 90 or more residues, or, the full length of the polypeptide, or, a polypeptide encoded by a nucleic acid of the invention, e.g., a nucleic acid comprising a sequence: (i) having at least 90% sequence identity to SEQ ID NO:1 over a region of at least about 100 residues, wherein the sequence identities are determined by analysis with a sequence comparison algorithm or by visual inspection, or, (ii) that hybridizes under stringent conditions to a nucleic acid as set forth in SEQ ID NO:1 or a complement thereof.

In one aspect, the polypeptide has an NFκB inhibiting activity. The invention provides methods of A method for inhibiting NFκB activity in a cell comprising the step of contacting the cell with the polypeptide according to the invention, or a fragment thereof.

The invention provides immobilized polypeptides of the invention. In one aspect, the polypeptides have an NFκB inhibiting activity, wherein the polypeptide comprises a sequence of the invention. In one aspect, the polypeptides comprise antibodies of the invention. The polypeptide can be immobilized on a cell, a metal, a resin, a polymer, a ceramic, a glass, a microelectrode, a graphitic particle, a bead, a gel, a plate or a capillary tube.

The invention provides arrays comprising an immobilized polypeptide of the invention, e.g., an antibody of the invention or a POP2 polypeptide of the invention. The invention provides arrays comprising an immobilized nucleic acid of the invention.

The invention provides isolated or recombinant antibodies that specifically bind to a polypeptide of the invention. The antibody can be a monoclonal or a polyclonal antibody. The invention provides hybridomas comprising an antibody that specifically binds to a polypeptide of the invention.

The invention provides methods of producing a recombinant polypeptide comprising the steps of: (a) providing a nucleic acid operably linked to a promoter; wherein the nucleic acid comprises a sequence of the invention; and (b) expressing the nucleic acid of step (a) under conditions that allow expression of the polypeptide, thereby producing a recombinant polypeptide. The methods can further comprise transforming a host cell with the nucleic acid of step (a) followed by expressing the nucleic acid of step (a), thereby producing a recombinant polypeptide in a transformed cell.

According to a further aspect, the invention provides a method for identifying a polypeptide having an NFκB inhibiting activity. This method comprises contacting a polypeptide of the invention, or a fragment thereof, with two or more molecules that multimerize or specifically associate in the presence of an NFκB inhibiting polypeptide; and detecting multimerization or specific association of the molecules; wherein multimerization or specific association of the molecules identifies the polypeptide as having an NFκB inhibiting activity.

According to a further aspect, the invention provides another method for identifying a polypeptide having an NFκB inhibiting activity. This method comprises contacting a polypeptide of the invention, or a fragment thereof, with a construct comprising an NFκB-responsive promoter operably linked to a reporter gene; and detecting the amount of reporter gene product produced; wherein an decrease in the amount of reporter gene product identifies the polypeptide as having an NFκB inhibiting activity.

The invention provides methods for identifying a polypeptide having an NFκB inhibiting activity comprising the following steps: (a) providing a polypeptide of the invention or a polypeptide encoded by a nucleic acid of the invention; (b) providing a construct comprising an NFκB-responsive promoter operably linked to a reporter gene; and (c) contacting the polypeptide of step (a) with the construct of step (b) and detecting the amount of reporter gene product produced, wherein an decrease in the amount product identifies the polypeptide as having an NFκB inhibiting activity. In one aspect, detecting the amount of reporter gene product produced comprises detecting the amount of reporter gene transcript, the amount of polypeptide encoded by the reporter gene, or, where the reporter gene encodes an enzyme, detecting the amount of the enzyme's product or substrate.

According to a further aspect, the invention provides a method of determining whether a test compound specifically binds to a polypeptide of the invention, or a fragment thereof. This method comprises contacting the polypeptide or fragment thereof with the test compound; and determining whether the test compound specifically binds to the polypeptide, thereby determining that the test compound specifically binds to the polypeptide.

According to a further aspect, the invention provides a method for identifying a modulator of an NFκB inhibiting activity. This method comprises contacting a polypeptide of the invention, or a fragment thereof, with a test compound; and measuring an activity of the NFκB inhibiting polypeptide; wherein a change in NFκB inhibiting activity measured in the presence of the test compound as compared to the NFκB inhibiting activity in the absence of the test compound provides a determination that the test compound modulates an activity of the NFκB inhibiting polypeptide. This method may further comprise providing two or more molecules that multimerize or specifically associate in the presence of an NFκB inhibiting polypeptide, wherein the NFκB inhibiting activity is measured by detecting an increase or decrease in the amount of multimerization or specific association of the molecules.

The methods can further comprise providing molecules that multimerize or specifically associate in the presence of an NFκB inhibiting polypeptide and wherein the NFκB inhibiting activity is measured by detecting an increase or decrease in the amount of multimerization or specific association of the molecules. In one aspect, a decrease in the amount of multimerization or specific association with the test compound as compared to the amount of multimerization or specific association without the test compound identifies the test compound as an inhibitor of NFκB inhibiting polypeptide activity. An increase in the amount of multimerization or specific association with the test compound as compared to the amount of multimerization or specific association without the test compound can identify the test compound as an activator of NFκB inhibiting polypeptide activity.

In one aspect, the test compound comprises a small molecule. The test compound can comprise an RNA. The RNA can comprise a small inhibitory RNA (siRNA) or an antisense RNA.

The invention further provides a method for identifying a polypeptide able to down-regulate the activity of an NFκB, said method comprising: contacting a polypeptide according to the invention, or a fragment thereof, with a reporter gene with activity determined by the activation state of an NFκB; and detecting a decrease in reporter gene activity; wherein a decrease in the amount of reporter gene activity identifies a polypeptide able to downregulate the activity of NFκB. In one aspect, detecting the amount of reporter gene activity comprises detecting the amount of reporter gene transcript, the amount of polypeptide encoded by the reporter gene, or, where the reporter gene encodes an enzyme, detecting the amount of the enzyme's product or substrate.

The invention further provides a method for determining a functional fragment of an NFκB inhibiting polypeptide. This method comprises deleting a plurality of amino acid residues from a polypeptide according to the invention to create a subsequence thereof; and testing the subsequence for an NFκB inhibiting activity, thereby determining a functional fragment of an NFκB inhibiting polypeptide.

The invention further provides a method of treating cancer, neurodegenerative disorders, arthritis or chronic inflammation, said method comprising administering a compound comprising (i) an amino acid sequence having at least 95% sequence identity to SEQ ID NO:2; or (ii) an amino acid sequence encoded by a nucleic acid comprising a sequence having at least 90% sequence identity to SEQ ID NO:1; wherein the polypeptide has an NFκB inhibiting activity.

The invention further provides a method of treating cancer, neurodegenerative disorders, arthritis or chronic inflammation, said method comprising modulating a polypeptide having NFκB inhibiting activity by administering a compound that binds to or modulates a polypeptide comprising (i) an amino acid sequence having at least 95% sequence identity to SEQ ID NO:2; or (ii) an amino acid sequence encoded by a nucleic acid comprising a sequence having at least 90% sequence identity to SEQ ID NO:1; wherein the polypeptide has an NFκB inhibiting activity.

The details of one or more aspects of the invention are set forth in the accompanying drawings and the description below. Other features, objects, and advantages of the invention will be apparent from the description and drawings, and from the claims.

All publications, patents, patent applications, and GenBank sequences, cited herein are hereby incorporated by reference.

BRIEF DESCRIPTION OF THE DRAWINGS

For a fuller understanding of the invention, reference should be made to the following detailed description, taken in connection with the accompanying drawings, in which:

FIG. 3 illustrates the POP2 cDNA (SEQ ID No: 1) and protein (SEQ ID No: 2) sequences. The sequence of the 3' untranslated region (3' UTR) is indicated as is the polyadenylation signal sequence (solid line).

FIG. 4 is an alignment of the POP2 protein sequence with 22 pyrin domains from human, mouse or viral proteins SEQ ID NOs: 1-28. Sequences longer than 100 amino acids were truncated. Shading represents conservation (either identity (black) or functionally similar (gray)) at given positions in greater than 50% of the aligned sequences. Bold numbers (relative to POP2) indicate the location of conserved residues shown to contribute to oligomerization (residues 11, 15, 18, 43, 68 and 84) or the position of the conserved basic patch typical of pyrin domains (XLXKFK; residues 22-27). Abbreviations not occurring in the text: MV (myxoma virus), YLDV (yaba-like disease virus), SPV (swine pox virus), SFV (Shope fibroma virus).

FIG. 11 shows the influence of POP2 on NF-κB nuclear localization. (A) HeLa cells were transiently transfected with 1 ug of GFP-POP2 and treated for 30 min with TNFa (20 ng/ml). (B) Cells were then fixed and stained using rabbit anti-human NF-κB-p65 and goat anti-rabbit IgG-PE. Fluorescence microscopy was performed to detect GFP-POP2, NF-κB-p65 and DNA (DAPI). (C) Localization of p65 was scored as mostly nuclear (N or Nuc.), nuclear and cytoplasmic (N/C or Nuc./Cyto.) and mostly cytoplasmic (C or Cyto.). Data are representative of two similar experiments.

DETAILED DESCRIPTION OF THE PREFERRED EMBODIMENT

Figure 1:
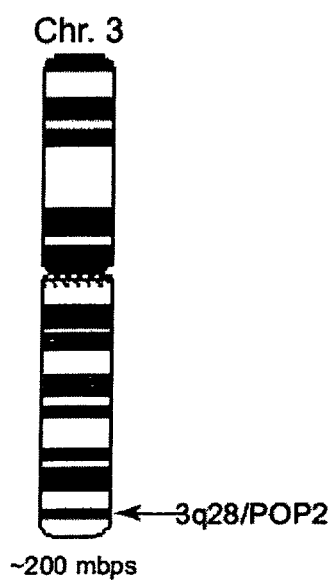
FIG. 1 is an ideogram of human chromosome 3 indicating the location of POP2. POP2 is encoded on human chromosome 3 (3q28).

The present invention relates to a novel gene product, POP2, that inhibits the transcription factor NF-kappaB (also referred to as NF-κB or NF-кB). NF-кB plays a broad role in biological processes including cell growth, cell death, and the production of cytokines as well as other expressed proteins. The technology described herein provides a means to inhibit and/or reduce the biological activities of NF-kappa B. The technology may also be able to modify the function of a broad class of human and mouse proteins known collectively by the names CATERPILLER, NOD, NALP, Pypaf, PAN, and NACHT. Potential uses include cancer chemotherapy, gene therapy, enhancing or modifying immune responses to bacterial, viral, fungal and protozoal infections, etc.

Pyrin domain (PYD) containing proteins are becoming increasingly appreciated for their roles in signaling and inflammation. The CLR (NLR, NALP) family members NALP1 and CIAS1/NALP3 are clearly involved in the formation of the inflammasome, which depends upon ASC (TMS1, PyCARD), an adapter protein repressed by promoter methylation in a variety of cancers, to recruit proinflammatory caspases. These CLRs recruit ASC via the interaction of the CLR PYD with that of ASC. In a similar fashion, Caspase1 is recruited by interactions between the CARD domains of ASC and Caspase1. Proteins encoding a single competing domain disrupting PYD or CARD interactions are attractive as regulators of these interactions and the Pyrin protein itself has been recently suggested as a regulator of ASC:Caspase-1 interactions. A CARD-only protein (COP) and several Pyrin-only proteins (POPs) have been described. COP inhibits the production of IL-1b by blocking oligomerization of Caspase-1, a role similar to that of two other CARD-only proteins ICEBERG and pseudo-ICE. A number of POPs are viral proteins contained in the genomes of pox viruses. One of these, M13L has recently been implicated as a virulence factor capable of inhibiting the production of IL-1b. The human genome contains at least two pyrin-only proteins (POPs), POP1, which inhibits ASC-dependent NF-кB activation and POP2, the subject of this study.

We teach a PYPAF2/NALP2 pyrin domain related gene on chromosome 3 in the human genome using of the human genome by BLAST search that we have named Pop2. The single exon, 274 bp gene encodes a 97 amino acid protein with sequence identity and predicted structure most consistent with that of a pyrin domain. Pop2 message is expressed principally in peripheral blood leukocytes and testis. Expression in purified leukocyte subpopulations is detectable, but weak (data not shown), suggesting that Pop2 is broadly expressed in immune cells. Pop2 was also detected at low levels in the monocytoid cell line THP-1, B and T cell lymphoma lines, but was more highly expressed in the erythroid leukemia line K562. This expression pattern is largely consistent with a role for POP2 in regulating CLR-dependent events in immune cells. CLR proteins also play a role in embryogenesis as illustrated by MATER, a non-pyrin CLR family member required for cell division in fertilized eggs. Likewise, mouse NALP14 is also believed to have developmental function. Expression of POP2 in testis may reflect a role for POP2 in regulating CLR-dependent events in development.

Not surprisingly, POP2 has a high degree of similarity to other pyrin domain proteins and, based on structural predictions, is likely to have a similar structure. Searches with the POP1 protein sequence failed to detect Pop2. Similarly, searches with the PYPAF2/NALP2 pyrin did not detect the Pop1 gene (data not shown), suggesting that it may be necessary to perform extensive searches with other PYDs to enumerate the full complement of human POPs. While POP1 is closely related to the ASC pyrin domain and inhibits the increased NF-кB activity seen upon ASC coexpression with either Pyrin or CIAS1, the structurally similar POP2 is more distantly related to the ASC PYD than POP1 and more closely resembles the CLR PYDs. Given this difference, POP2 might have the potential to be a specific competitor for CLR PYDs, while POP1 is more specific for ASC. However, studies addressing the binding affinities of different PYD:PYD combinations have yet to be performed.

Considering a relatively small size (~12 kDa), it is not surprising that POP2 is expressed throughout the cell. Curiously, POP2 displays nuclear concentration in nearly a quarter of expressing cells. The reason for this is unclear, but suggests that POP2 may contain a nuclear localization sequence (NLS). Curiously, a consistent feature of pyrin domains is a basic patch (KKFK) near the N-terminus that is similar to the SV40 NLS. However, while the CLR proteins CIAS1 and Monarch as well as POP1 and ASC all have an SV40 NLS-like sequence (KKFK) in their pyrin domains, POP2 has the less likely NLS sequence (SKFK). Nevertheless, CIAS1 and Monarch appear to be exclusively cytoplasmic, suggesting that this sequence may not be an NLS. Similarly, the prototypic PYD protein, Pyrin (marenostrin) which is mutated in Mediterranean Fever, was initially believed to function in the nucleus. Interestingly, Pyrin nuclear localization was leptomycin B insensitive and two putative NLS sequences were dispensable. Subsequently, the potential nuclear role of Pyrin has been overshadowed by its ability to interact with ASC. Despite these difficulties, some pyrin domain proteins are clearly nuclear proteins. IFI16, an interferon induced protein, and AIM2 which is activated in melanoma cells, both contain a HIN-200 DNA binding domain and may play roles in transcription.

Pyrin-containing proteins are reported to have diverse effects on the function of NF-кB. Consistently, pathogen recognition by CLR proteins is thought to lead to NF-кB activation via RIP2 and IKK. This function is further supported by the ability of some CLR pyrin domains to cooperatively activate NFкB when expressed as truncations. However, other CLR pyrin domains, such as that of PAN2/PYPAF4 and PYPAF2/PAN1, inhibit NF-кB, suggesting that CLRs may perform both proinflammatory and anti-inflammatory roles. More in keeping with PAN1/2, both POP1 and POP2 appear to have NF-кB inhibiting properties. POP2 inhibits both TNFa-induced NF-кB activity in a variety of cells and the transcriptional activity of transiently transfected p65. The mechanisms leading to NF-кB inhibition are unclear, but both PAN2 and POP1 have been reported to interact with IKKα which may affect the downstream phosphorylaion of IкBα. In these studies, the lack of IKK activity correlated with POP1 or PAN2 inhibition of TNFa-induced NF-кB activity. While POP2 can inhibit TNFa-induced NF-кB activation, it also inhibits activation seen following transfection of the active p65 subunit. In addition, we observe that POP2 expression does not necessarily prevent nuclear import of NF-кB, but may alter nuclear distribution or accumulation as evidenced by POP2 expressing cells with either less abundant or redistributed nuclear NF-кB. These experiments suggests that inhibition occurs downstream of IKK at the nuclear level. Whether these patterns result from a relatively direct inhibition of p65 or could in some fashion involve IKK remains to be seen.

Figure 12:
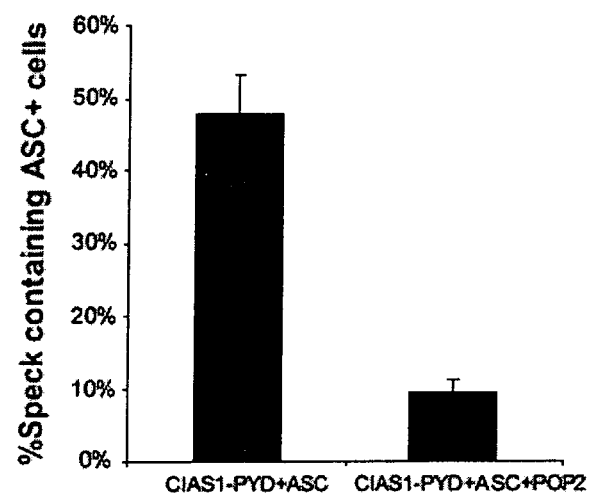
FIG. 12 shows the blockage by POP2 of CIAS1:ASC speck formation. HeLa cells were transiently transfected with Myc-ASC alone or together with CIAS1-PYD or CIAS-PYD and GFP-POP2. Cells were stained with anti-Myc and goat anti-mouse IgG-PE. Over 500 ASC positive cells were counted for each condition in a total of three transfections. The mean percentage of ASC expressing cells containing specks under each condition is shown +/−SEM. Expression of ASC alone does not yield specks.

Pyrin domains can also form complexes with the pyrin-CARD protein ASC. The interaction of Pyrin with ASC results in redistribution to a perinuclear speck that may be associated with proapoptotic cells. Further, the PYDs of the CLR proteins NALP1, NALP2, and NALP3 recruit ASC and Caspase-1 to form the proIL-1b and proIL-18 converting inflammasome complex. Accordingly, many CLR proteins, but not all, associate with ASC in a perinuclear speck indistinguishable from the initially described pyrin speck. Like POP1 and certain pyrin-containing CLR proteins, POP2 also forms specks when coexpressed with ASC (FIG. 12). It remains uncertain why some pyrin domains are able to associate with ASC and others are not. But, these PYD interactions again raise the possibility that speck and/or inflammasome formation could be regulated by single domain proteins such as COP, POP1, and POP2. In a speck formation assay using the pyrin domain of CIAS1/NALP3, POP2 is able to nearly abolish the interaction of CIAS1 and ASC. This strongly supports the hypothesis that ASC structures such as the speck and inflammasome are targets for regulation by pyrin or CARD-only proteins.

The implications for pyrin-only protein mediated regulation of ASC interactions are notable. The interaction of ASC with pyrin proteins is associated with a proapoptotic state (speck formation) and with the inflammatory response to pathogen associated molecular patterns, such as muramyl dipeptides and dsRNA through both activation of NF-κB dependent cytokine transcription and cleavage of preformed IL-1b and IL-18 precursors via CLR containing inflammasomes. Proteins, such as POP2, that can disrupt or otherwise impede these processes might have broad impact on cellular development, survival, or homeostasis by contributing to the control of apoptotic programs. With respect to innate immune responses, understanding of mechanisms attenuating inflammatory responses is limited. Pyrin-only proteins may represent a mechanism for restraining proinflammatory activation events by slowing the inflammasome formation, for terminating inflammatory signals and processes by limiting the duration of inflammasomes, or both. Mutations in CIAS1/NALP3 lead to a spectrum of inflammatory diseases. POP2 disruption of ASC:CIAS1/NALP3 interactions could be used to ameliorate inflammation in these individuals. Further, POP2 shows the ability to independently inhibit NF-κB. This has broad implications for controlling NF-κB activity to induce or block gene expression, to prevent or favor apoptosis, etc. A better understanding of the mechanistic properties of such molecules capable of modulating NF-κB may ultimately provide alternative therapeutic strategies for the broad spectrum of diseases associated with sustained NF-κB activity including Alzheimer's, autoimmune diseases, and cancer.

Discovery and Cloning of POP2

Figure 2:
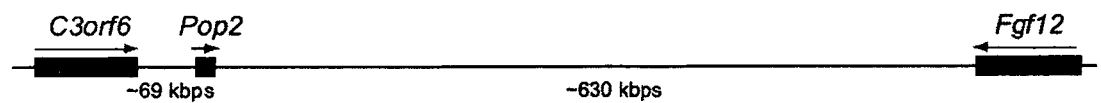
FIG. 2 is diagram of the portion of contig NT_152138 containing POP2, the relative positions of C3orf6, POP2 and Fgf12 are shown by filled boxes, distances are approximate, arrows indicate the direction of transcription.

Using the amino acid sequences of previous described PYDs (e.g. from PYPAF1/Monarch, PYPAF2/NALP2, etc) in TBLASTN searches revealed a novel sequence, a 274 basepair, single exon gene coding for 97 amino acids corresponding to contiguous sequence LOC152138 in the human genome on the distal teleomeric end of chromosome 3 (3q28) (FIG. 1). The deduced amino acid sequence has 78% similarity (67% identity and 1e-25 E-value) to the PYD of PYPAF2 (data not shown). Despite the presence of an in-frame stop codon, we considered that this single exon might belong to a larger gene. Genomic analysis to determine additional predicted exons or expressed sequence tags (ESTs) in reasonable proximity (<+/-50 kbps) to this exon were uninformative. The closest identified upstream gene (68.9 kbps away) is C3orf6 (FIG. 2), a differentially spliced 12-exon gene yielding a 306 and a 482 amino acid protein potentially involved in spastic paraplegia. Downstream, the fibroblast growth factor 12 gene, Fgf12, is >630 kbps distant. The gene was isolated from DNAse treated total RNA and cloned into pcDNA3 containing either a FLAG or Myc-epitope tag. The sequence of the resulting cDNA was identical to that in the NCBI database (FIG. 3). Determination of the 3' end of the gene from polyA+ mRNA reveals no evidence of splicing to a downstream exon and that the coding region terminates at the in-frame stop codon. BLAST searches of the mouse and rat genome yielded no similar murine gene, although the equivalents of C3orf6 were detected in both databases (data not shown). As anticipated, transfection of 293 cells with the Myc-tagged constructed yielded an approximately 12 kilodalton protein (not shown). Given the high degree of similarity to the PYPAF PYD, we have coined the name pyrin-only protein 2 (POP2).

POP2 has a Pyrin Domain Most Similar to CLR Pyrins

Figure 4:
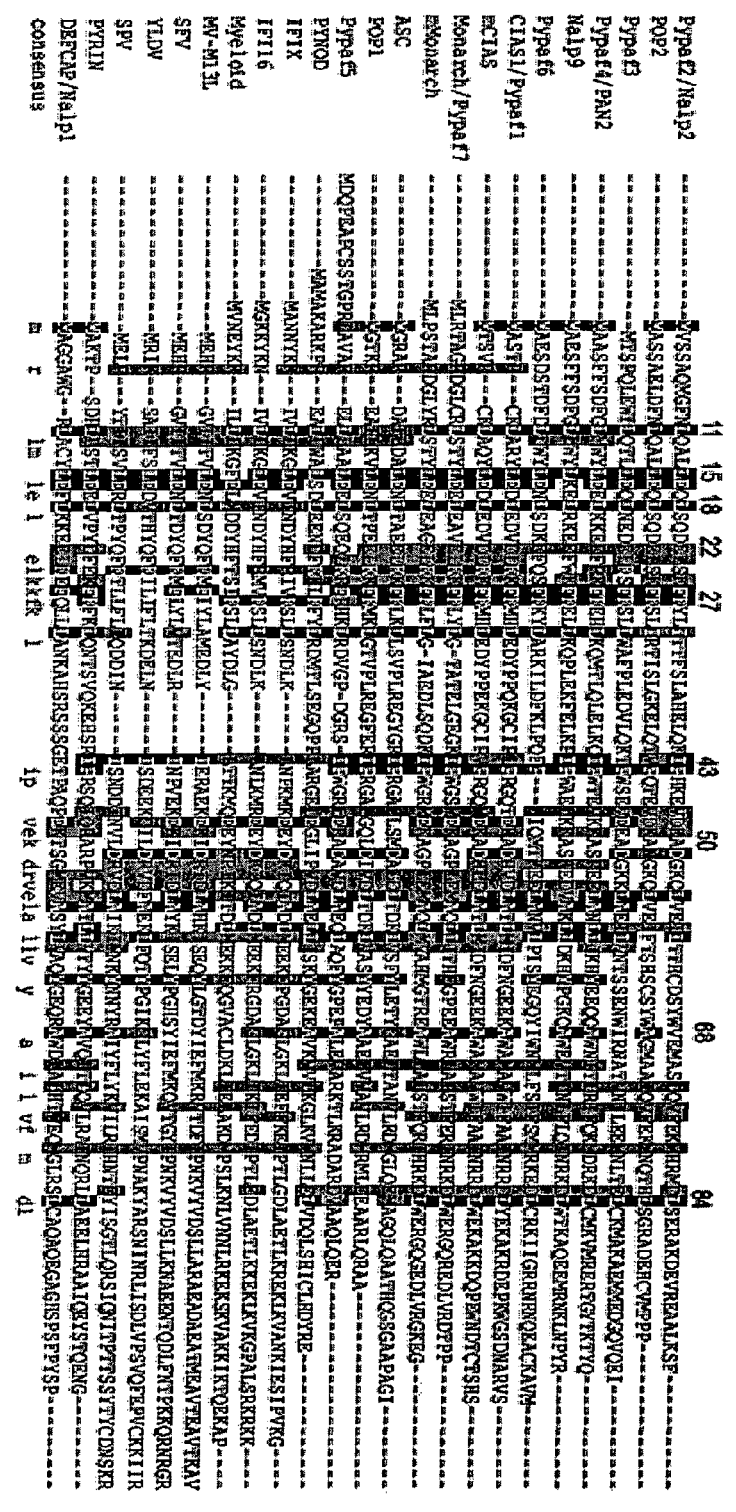
Figure 5:
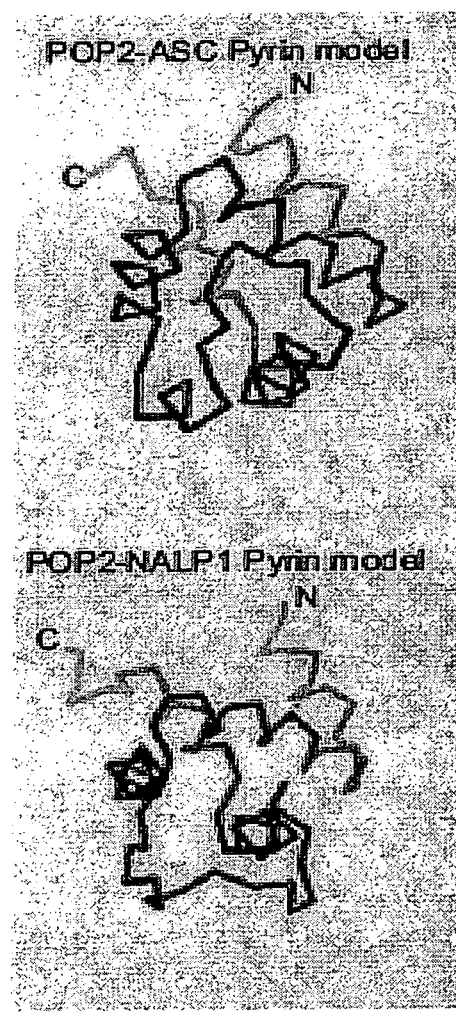
FIG. 5 illustrates the backbone structural diagram of POP2 structural predictions based on ASC (top panel) or NALP1 (bottom panel) pyrin domains. Structures were generated from POP2 primary sequence using the 3D-PSSM algorithm at the Imperial College of Science, Technology, and Medicine (London). Both structures are high confidence models (>90%). N, indicates amino-terminus. C, indicates carboxy-terminus.
Figure 6:
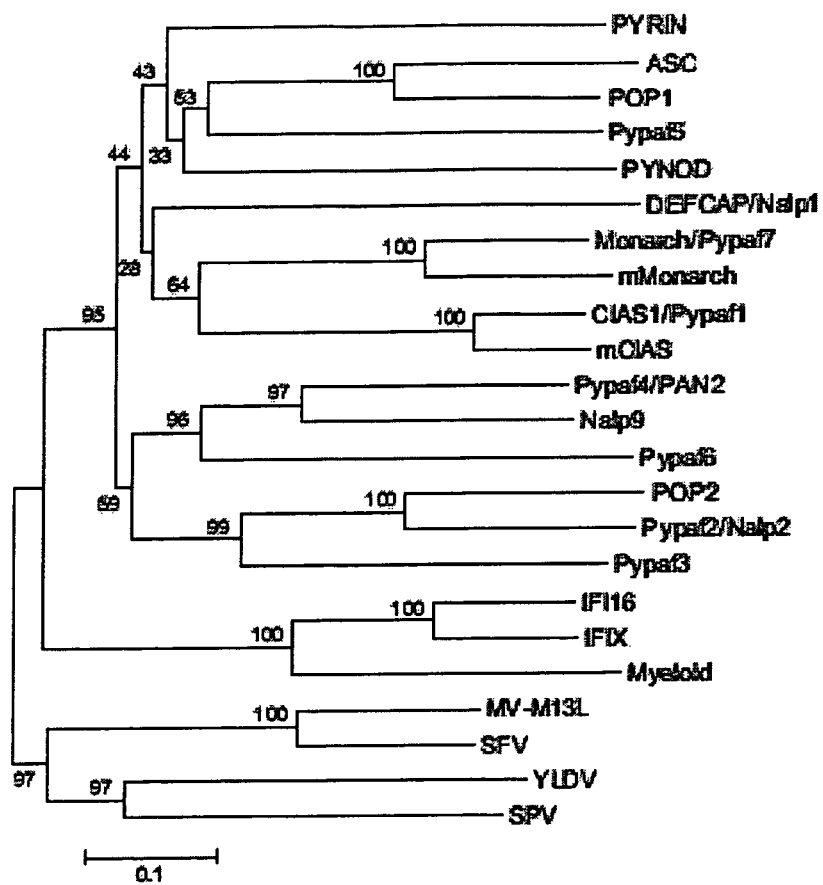
FIG. 6 illustrates the phylogenetic relationships between POP2 protein and the pyrin sequences shown in FIG. 4. Numbers indicate bootstrap values (% of 1000 replicates) reflecting the degree of relatedness between clustered sequences. Viral pyrin proteins are clustered as an outgroup.

Consistent with the high degree of identity with the PYPAF2 PYD, multiple alignments using the POP2 protein sequence revealed a high homology to other PYDs (FIG. 4). Residues L11, L15, L18, P43, A50, A68 and L84, thought to play an important role in homotypic PYD oligomerization, and the sequence motif XLXKFK are generally conserved in PYDs. These residues and sequences are likewise conserved in POP2. Threading analysis of the POP2 protein sequence using the 3D-PSSM algorithm returns two high confidence (>90%) models based on the pyrin domains of ASC and NALP1 (FIG. 5). Phylogenetic analysis indicates that the POP2 is more similar to PYDs of the CLR family than to POP1 or ASC PYDs (FIG. 6). This strongly suggests this gene may have originated from a CLR-PYD gene duplication event and is likely not a paralog of POP1. These findings together demonstrate that POP2 encodes a single, bona fide pyrin domain, the second such gene in the human genome.

POP2 is Primarily Expressed in PBLs

Figure 7:
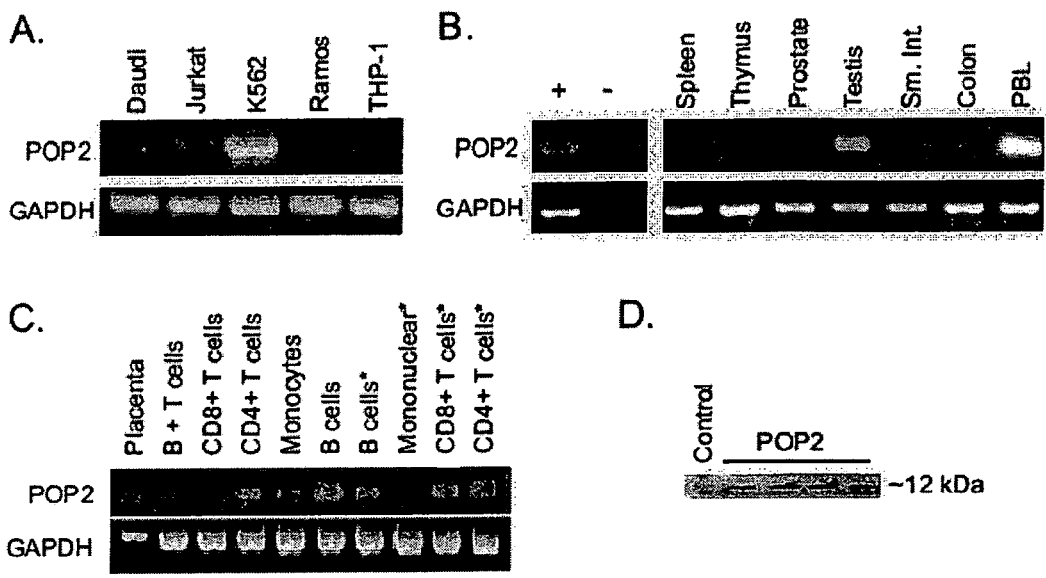
FIG. 7 shows the expression of POP2. (A) DNAse-treated total RNA was prepared from the indicated human cell lines and subjected to RT-PCR using POP2-specific primers. GAPDH-specific primer amplified controls are shown. (B) POP2 and GAPDH cDNA was amplified from a panel of normal tissues. K562 cDNA is shown as a positive control. Amplification without template cDNA was used as a negative control. (C) POP2 and GAPDH cDNA from a human blood fraction panel was amplified as in B. (D) HEK293 cells were transiently transfected with 1 µg of Myc-tagged ASC (control) or POP2 (indicated lanes) and immunoblotted with anti-Myc antibody and goat-anti-mouse-HRP.

To determine the expression pattern of POP2, we performed RT-PCR using mRNA isolated from various cell lines (FIG. 7A). POP2 mRNA was readily detected in the K562 (human erythroblastoid leukemia) cell line. Lower amounts of POP2 were detected in the Jurkat T cell line, Ramos B lymphoma, and the monocytoid/macrophage line THP-1. Relative to GAPDH, POP2 was more abundant in K562. The expression of POP2 mRNA in primary cells was examined using a normal human tissue cDNA panel. A product of the expected size was readily observed in peripheral blood leukocytes (PBL) with some expression in testis (FIG. 7B), although expression appeared greater in PBL. An appropriately sized band, weaker than seen in testis was observed in both thymus and spleen. Next, we surveyed a human blood fraction panel to determine which specific PBL cell populations express POP2 (FIG. 7C). POP2 mRNA was detected at low levels in all of the samples included in the panel. Since LPS treatment alters the expression of PYPAF2 in THP1 cells, we stimulated THP1 with LPS (10 ng/ml; 24 hours). No changes in POP2 expression were observed (data not shown). A number of important leukocyte populations are not represented in the panel, including granulocytes, macrophages, NK cells, and dendritic cells. With the exception of granulocytes these leukocytes are not typically present in peripheral blood in significant numbers. Collectively, these data support broad expression of POP2 in hematopoietic and immune cell lines and in primary leukocytes. An N-terminal MYC-tagged cDNA clones of POP2 was generated and HEK-293 cells were transfected. Lysates from transient transfectants yielded the expected ~12 kDa protein as demonstrated by anti-Myc immunoblot (FIG. 7D).

POP2 Localizes to Nuclear and Cytoplasmic Compartments

Figure 8:
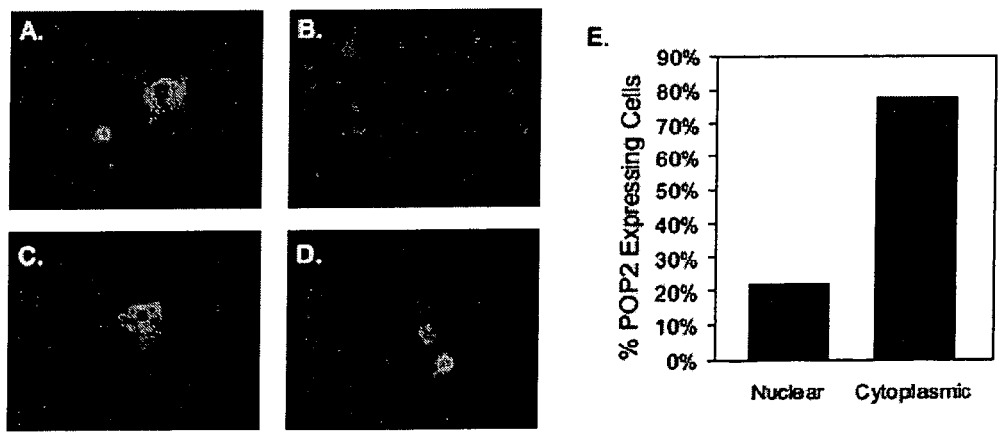
FIG. 8 shows localization of POP2 to both nuclear and cytoplasmic compartments. (A)-(D) COS-7 cells were transfected with 2 µg FLAG-tagged POP2 and visualized with anti-FLAG(M5) and goat anti-mouse FITC by fluorescence microscopy. A., C., and D. show representative fields. B. DAPI counterstained image of A. (E)>100 cells (POP2$^+$) from two independent transfections were counted to quantitate the proportions of cells with the indicated staining pattern. Cytoplasmic, includes cells with either exclusive cytoplasmic staining or a combination of nuclear and cytoplasmic. Nuclear, includes only those cells with predominating nuclear POP2.

Expression of POP2 was also examined by immunofluorescence in HeLa cells to determine the sub-cellular distribution of POP2. POP2 was observed to be either largely cytoplasmic, present in both cytoplasm and nucleus (with little or easily observed nuclear expression) or concentrated principally in the nucleus (FIG. 8A-D). Most POP2 expressing cells display the cytoplasmic or more evenly distributed pattern; however a substantial minority (20%) display concentrated nuclear expression (FIG. 8E). The presence of POP2 in both the cytoplasm and the nucleus is consistent with its size and suggests that POP2 may function in either, or both, compartments. The nuclear concentration of POP2 suggests the presence of at least one nuclear localization signal sequence (NLS), although no canonical NLSs are present in the coding sequence.

POP2 Inhibits NF-κB Activity

Figure 9A:
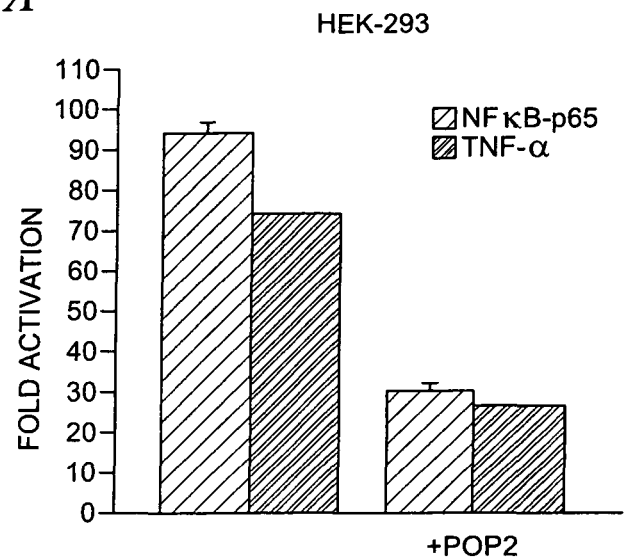
FIG. 9 shows POP2 inhibition of TNF-α induced and exogenous p65-induced NF-κB activity. (A)-(C) HEK-293T (A) HeLa (B) and COS-7 (C) cells were transiently transfected with either 1 µg pcDNA3 or 1 µg POP2 and cotransfected with p65 (0.1 µg) or treated 24 hours later with TNF-α(10 ng/ml; 30 min). Activation of the NF-κB -Luc reporter was measured (relative fold activation (relative to pcDNA3 control) +/−SEM, representative of 3 experiments). (D) COS-7 cells were transiently transfected with either pcDNA3 or 100 ng NF-κB -p65 and increasing amounts of POP2 (total DNA=1.1 µg) and activation of an NF-κB -Luc reporter was measured (fold activation relative to pcDNA3+/−SEM, representative of 3 identical experiments). (E) Transfection of HEK-293 cells with POP2 (1 µg) does not inhibit the CMV promoter-driven pGL3-control luciferase reporter. FIG.
Figure 9B:
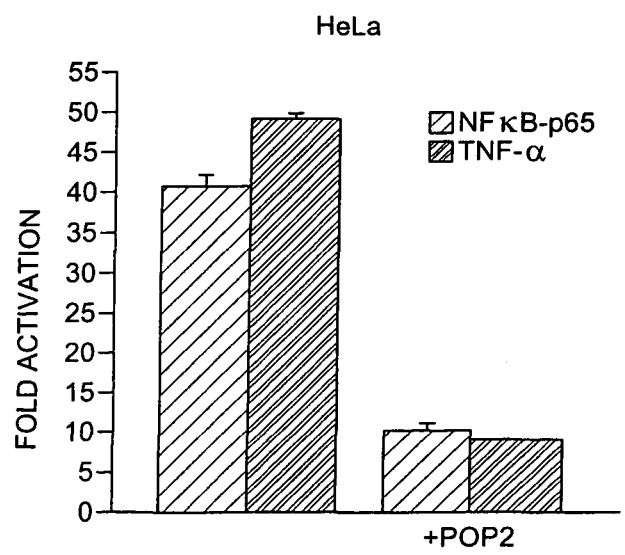
Figure 9C:
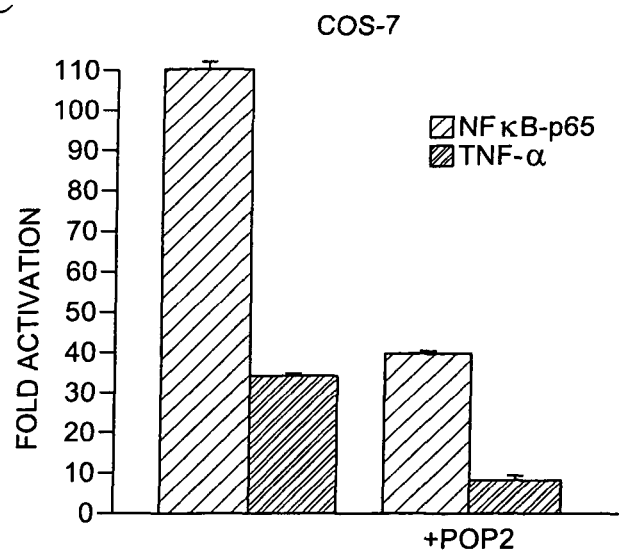

Knowing that POP2 is expressed in immune cells and that PYD-containing proteins are implicated in inflammatory disorders, led us to hypothesize that POP2 might function in the regulation or exacerbation of innate immune responses. Due to NF-κB's recognized role as a pro-inflammatory inducer, we therefore investigated if POP2 was affecting NF-κB activity due. HEK-293 cells were transiently co-transfected with the 3X-NF-κB-Luc reporter and POP2 cDNA. 18 hours later the cells were stimulated with TNF-α (10 ng/mL for 30 min) and whole-cell lysates analyzed for luciferase activity (FIG. 9A). A close to 3-fold inhibition of TNFα-stimulated NF-κB was observed following in POP2 transfectants, indicating that POP2 interferes with NF-κB signaling downstream of the TNFR. These results were confirmed in HeLa and COS-7 cells with highly concordant results (FIGS. 9B and C).

Figure 9D:
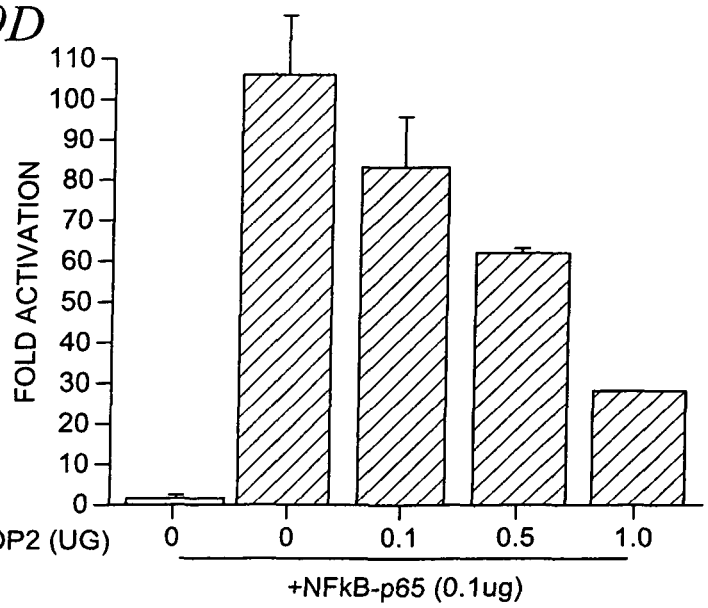
Figure 9E:
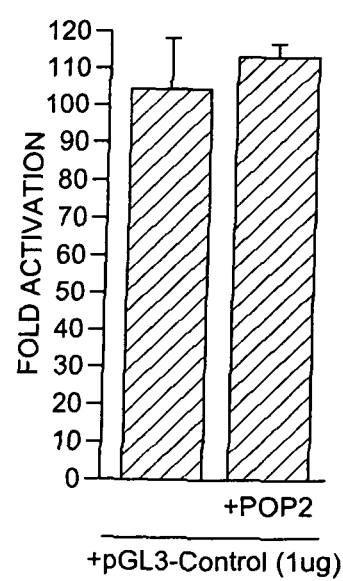

The ability of POP2 to block TNFα-mediated NF-κB activation suggests that POP2 is involved in down-regulating the NF-κB signaling cascade. To determine the point where POP2 affects the pathway we tested the factors involved in triggering the activating signal beginning with the p65 subunit of NF-κB at the distal end of the cascade. Luciferase assays were performed using lysates from HEK-293 cells cotransfected with increasing amounts of POP2, NF-κB-Luc reporter and 'active' p65 (FIG. 9D). A dose-dependent inhibition of p65 NF-κB was observed with the highest amounts of transfected POP2 yielding results comparable to those where TNFα was used suggesting that POP2 inhibits distal NF-κB signals activating signal by affecting p65. When a CMV-promoter driven pGL3-control expression plasmid was co-transfected along with POP2 no suppression was observed, indicating that POP2 is not a general inhibitor of transcription (FIG. 9E).

POP2 Colocalizes with ASC in Perinuclear Specks.

Figure 10:
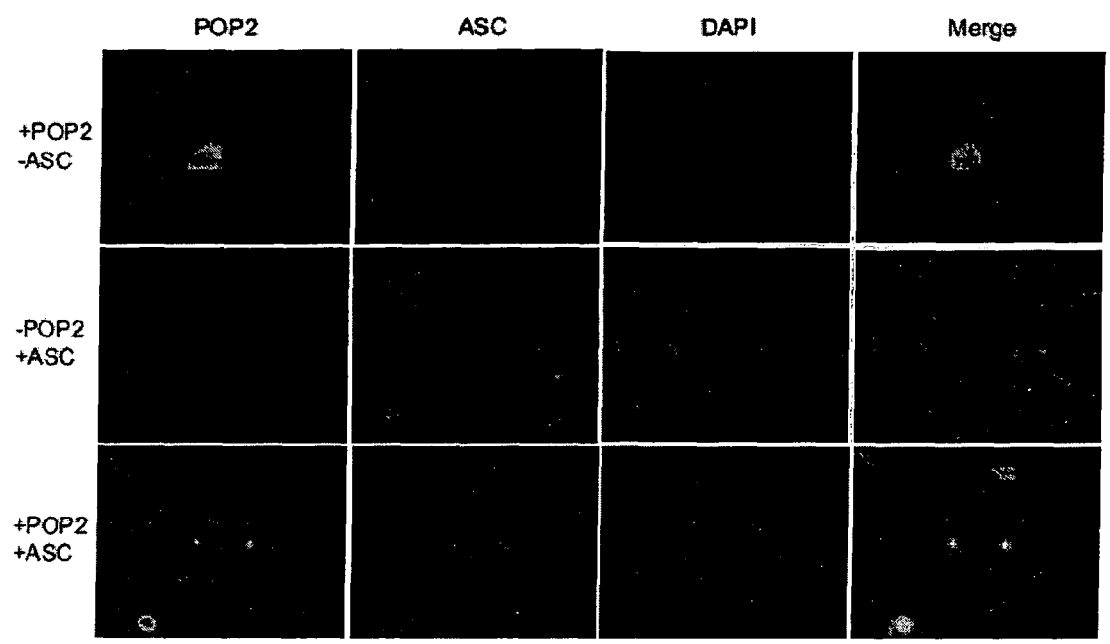
FIG. 10 shows POP2 co-localization with ASC in perinuclear specks. HeLa cells were transiently transfected with either GFP-POP2 or Myc-ASC, or both, fixed at 48 hours and stained using mouse anti-Myc antibody. Localization was determined by indirect immunofluorescence with goat anti-mouse IgG PE-conjugated secondary antibody. Nuclei were detected by DAPI counterstaining.

Some members of the PYD family, including Pyrin and a number of CLRs, form a perinuclear structure (speck) by interacting with ASC, while others do not. CLR activation of NF-κB appears to correlate with an ability to interact with ASC and the pyrin domain of PAN2/PYPAF4 which inhibits NF-κB fails to form a speck in the presence of ASC. However, POP1 interacts with ASC, but inhibits NF-κB. To determine if POP2 colocalizes with ASC in a speck, immunofluorescence staining was performed on HeLa cells co-transfected with GFP-POP2 and Myc-ASC (FIG. 10). Cells receiving GFP-POP2 alone displayed a nuclear and cytoplasmic staining pattern consistent with that of FLAG-POP2. No GFP-POP2 containing specks were observed. Cells receiving ASC alone evidenced concentrations of ASC in the cytoplasm, but no discrete specks. Co-transfection of GFP-POP2 together with ASC however, resulted in the formation of perinuclear specks containing both ASC and GFP-POP2. Our results indicate that POP2 interacts with ASC and is capable of participating in speck formation.

POP2 Inhibits the Nuclear Accumulation of p65 NF-κB.

Since POP2, like POP1, was able to both associate with ASC and inhibit NF-κB, we next considered how POP2 might inhibit NF-κB. Another pyrin containing protein, CIAS1, inhibits p65 NF-κB by preventing the nuclear translocation of p65 (23). We thus considered the possibility that POP2 might function similarly. To facilitate visualization of POP2, a GFP-POP2 fusion was expressed in HeLa cells. Following TNFa treatment, less nuclear p65-NF-κB was observed in GFP-POP2 expressing cells (FIG. 11A). Either a rearrangement in p65 NF-κB subcellular location (from diffuse nuclear to perinuclear) or a reduction of nuclear p65 was observed (FIG. 11A and 11B). To quantitate the observed changes, more than 100 cells were examined for their p65 localization pattern. As shown in FIG. 11C, greater than 90% of the TNF-treated cells without POP2 had strong nuclear expression of p65. In the presence of POP2, only 40% of POP2 expressing cells had nuclear p65. The remaining 60% of the POP2 expressing cells had p65 staining in both the cytoplasm and the nucleus. These results suggest that POP2 alters p65 accumulation (or distribution), but likely does not simply block p65 nuclear import.

POP2 Competes with the CIAS1 Pyrin Domain

Pyrin-only proteins have the potential to interfere with PYD interactions by acting as a competitor. Since POP2 interacted with ASC, it seemed plausible that this interaction might prevent association of ASC with CLR PYD proteins. To determine if POP2 is able to disrupt a functional ASC:CLR interaction we tested its ability to disrupt the recruitment of the CIAS1 PYD to specks by ASC (FIG. 12). Cotransfection of a pyrin only CIAS1 construct (CIAS1-PYD) and ASC into HeLa cells leads to the formation of specks in nearly 50% of cells expressing ASC. Transfection of ASC alone does not yield specks. Curiously, when POP2 is coexpressed, only around 10% of the ASC expressing cells have specks, despite POP2's ability to form specks independently. The relative absence of speck formation in cells expressing CIAS1, POP2, and ASC suggests that CIAS1 and POP2 pyrin domains interact, thereby preventing the formation of an ASC-containing speck. The finding implies that, in addition to inhibiting NF-κB, POP2 may act as an inhibitor of complex assemblies involving ASC and CLR proteins, such as the CIAS1 and NALP1 inflammasomes.

Materials and Methods

Bioinformatics

TBLAS TN searches of the human genome were performed at NCBI (Bethesda, MD) using the N-terminal-100-amino-acid sequence of PYPAF2 (pyrin-containing Apaf-1-like protein 2) as a query. Multiple alignments of different pyrin domains and phylogenetic analysis were done with CLUSTALW (EMBL-European Bioinformatics Institute, Cambridge, England) and MEGA2 (Molecular Evolutionary Genetic Analysis, The Biodesign Institute at Center for Evolutionary Functional Genomics, Tempe, AZ). Tertiary structure prediction using ASC and NALP1 pyrin domains as a template was completed using the London Imperial College of Science, Technology and Medicine web-server, 3 D-PSSM.

Reagents and Antibodies

Recombinant human TNFα and goat anti-mouse IgG1-FITC were purchased from BD Pharmingen (San Diego, Calif.). Mouse-anti-FLAG M5 monoclonal antibody and goat anti-mouse horseradish-peroxidase-conjugated IgG1 antibody were purchased from SIGMA (Saint Louis, Mo.). Mouse-anti-myc tag IgG1 monoclonal antibody was purchased from Upstate (Lake Placid, N.Y.), rabbit p65 polyclonal IgG from Santa Cruz Biotechnology (Santa Cruz, Calif.), and Alexa Fluor 594® goat anti-rabbit IgG (H+ L) from Molecular Probes (Eugene, Oreg.).

Cloning and RT-PCR

A cDNA encoding POP2 was amplified from total RNA from the B-cell line Ramos by RT-PCR using the RT One Step Kit (QIAGEN, Hilden, Germany) with the primers (forward 5'-aaccgcggatggcatcttctgcagag-3' (SEQ ID No. 3) and reverse 5'-agcttatggcatcttctgcagag-3' (SEQ ID No. 4) designed to obtain POP2 cDNA (SEQ ID No. 5) flanked by Hind III and Xho I restrictions sites. Subsequently, POP2 was cloned into the pCDNA 3.1 vector containing an N-terminal Flag or Myc epitope. For POP2 mRNA detection, total RNA was isolated from Daudi, Ramos (B-cell lymphomas), Jurkat (human T-cell leukemia), THP-1 (human monocytic cell line) and K562 (human erythroid cell line) using the RNeasy RNA Isolation Kit (QIAGEN) and reverse transcribed and amplified with the One-Step RT-PCR Kit (QIAGEN). The same procedure was performed on total RNA from multiple human tissues (MTCC Panel I) and human blood fractions (MTC panel), both from BD Biosciences (Palo Alto, CA). Primers for glyceraldehyde-3-phosphate dehydrogenase (GAPDH) were used as a control.

Cell Culture, Transfection and Luciferase Assays

HEK 293, HeLa and COS-7 cells (American Type Culture Collection, Manassas, Va.) were cultured in either Dulbecco's modified Eagle's (DMEM) or RPMI medium supplemented with 10% heat-inactivated fetal bovine serum, 5% L-glutamine and 0.1% penicillin/streptomycin. Cells were passed every 3-4 days. Cell number and viability was determined by trypan blue exclusion. For transient transfection assays, cells were plated onto 6-well plates ($2 \times 10^5$ cells per well) and incubated at 37° C., 5% $CO_2$ and 95% humidity for sixteen hours. Transfection was carried out with FLAG-POP2 (different quantities), 100 ng of pNF-κB-Luc (a 3×NF-κB-driven firefly luciferase reporter), and either 100 ng of NF-κB-p65 using FuGene6 (3 μl:1 μg of DNA, Roche, Basel, Switzerland), or stimulated with varying amounts of TNF-α twenty-four hours posttransfection. The total amount of DNA in each transfection was kept constant (1100 ng/well) by the addition of empty vector (pcDNA3). Cell lysates were prepared using 200 μl of lysis buffer (1M Tris pH 7.4, 1M NaCl, 10 mM EDTA, 1% Triton X), and luciferase was quantitated according to standard protocol on a VICTOR™ Light Luminescence Counter (Wallac Co., Turku, Finland).

Western Blotting

Western blotting for Flag- and Myc-tagged proteins was performed essentially as described in Springer, T. A. 1999. Analysis of proteins. In Current Protocols in Molecular Biology, Vol. 2. I. M. A. R. B. R. E. K. D. D. M. J. G. S. J. A. S. a. K. Struhl, ed. John Wiley & Sons, Inc., New York, N.Y., p. 10.16.1. Following transfection and lysis, equal amounts of protein were separated on an SDS-PAGE (15% polyacrylamide) gel, for 40 min at 200 volts, transferred to nitrocellulose (0.2 μm) for 1 hour at 110 volts and immunoblotted with either α-FLAG antibody (M5, Sigma; 1:5000) or α-myc antibody (1:7500). Bound M5 or α-myc was detected with goat anti-mouse IgG1-horseradish peroxidase (SouthernBiotech; 1:7500) and visualized on Autoradiography film (Midwest Scientific, St. Louis, Mo.) using Supersignal WestPico HRP Detection Reagents (Pierce Biotechnology, Rockford, Ill.).

Immunofluorescence Microscopy

COS-7 and HeLa cells were cultured overnight in two-chamber slides at a density of $8 \times 10^4$ cells per chamber. Cells were transiently transfected with 1 μg of pcCDNA3 as negative control and either 1 μg GFP-POP2, 1 μg of FLAG-CIITA or 1 μg of MYC-ASC as positive controls. Either 1 μg of FLAG-POP2, 1 μg of Myc-POP2, 1 μg of NF-κB-p65 or 1 μg of Myc-ASC was used. After 18 hours, cells were fixed with a 3:2 Acetone:PBS solution, washed with PBS (1% BSA) and blocked with PBS (1% BSA, 10% NGS). Cells then were incubated for 1 hour at room temperature with mouse anti-FLAG or anti-Myc antibody or rabbit anti p65 polyclonal IgG, washed with PBS (1% BSA) and incubated (1 hr, RT) with either goat anti-mouse IgG1-FITC, goat anti-mouse IgG1-PE or goat anti-rabbit IgG-PE. Finally, cells were washed three times with PBS, stained with DAPI and visualized using a fluorescence microscope.

General Techniques

The nucleic acids used to practice this invention, whether RNA, iRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

The invention provides oligonucleotides comprising sequences of the invention, e.g., subsequences of the exemplary sequences of the invention. Oligonucleotides can include, e.g., single stranded poly-deoxynucleotides or two complementary polydeoxynucleotide strands which may be chemically synthesized.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immuno-electrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), nucleic acid or target or signal amplification methods, radiolabeling, scintillation counting, and affinity chromatography.

Obtaining and manipulating nucleic acids used to practice the methods of the invention can be done by cloning from genomic samples, and, if desired, screening and re-cloning inserts isolated or amplified from, e.g., genomic clones or cDNA clones. Sources of nucleic acid used in the methods of the invention include genomic or cDNA libraries contained in, e.g., mammalian artificial chromosomes (MACs), human artificial chromosomes, yeast artificial chromosomes (YAC);

bacterial artificial chromosomes (BAC); P1 artificial chromosomes, cosmids, recombinant viruses, phages or plasmids.

The invention provides fusion proteins and nucleic acids encoding them. A polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification.

Transcriptional Control Elements

The nucleic acids of the invention can be operatively linked to a promoter. A promoter can be one motif or an array of nucleic acid control sequences which direct transcription of a nucleic acid. A promoter can include necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

Expression Vectors and Cloning Vehicles

The invention provides expression vectors and cloning vehicles comprising nucleic acids of the invention, e.g., sequences encoding the proteins of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors of the invention can include chromosomal, non-chromosomal and synthetic DNA sequences. Large numbers of suitable vectors are known to those of skill in the art, and are commercially available.

The nucleic acids of the invention can be cloned, if desired, into any of a variety of vectors using routine molecular biological methods. To facilitate cloning of amplified sequences, restriction enzyme sites can be "built into" a PCR primer pair.

The invention provides libraries of expression vectors encoding polypeptides and peptides of the invention. These nucleic acids may be introduced into a genome or into the cytoplasm or a nucleus of a cell and expressed by a variety of conventional techniques, well described in the scientific and patent literature. See, e.g., Sambrook, Tijssen or Ausubel. The vectors can be isolated from natural sources, obtained from such sources as ATCC or GenBank libraries, or prepared by synthetic or recombinant methods.

In one aspect, the nucleic acids of the invention are administered in vivo for in situ expression of the peptides or polypeptides of the invention. The nucleic acids can be administered as "naked DNA" (see, e.g., U.S. Pat. No. 5,580, 859) or in the form of an expression vector, e.g., a recombinant virus. The nucleic acids can be administered by any route known in the art.

The term "expression cassette" as used herein refers to a nucleotide sequence which is capable of affecting expression of a structural gene (i.e., a protein coding sequence, such as a polypeptide of the invention) in a host compatible with such sequences. Expression cassettes include at least a promoter operably linked with the polypeptide coding sequence; and, optionally, with other sequences, e.g., transcription termination signals. Additional factors necessary or helpful in effecting expression may also be used, e.g., enhancers. "Operably linked" as used herein refers to linkage of a promoter upstream from a DNA sequence such that the promoter mediates transcription of the DNA sequence. Thus, expression cassettes also include plasmids, expression vectors, recombinant viruses, any form of recombinant "naked DNA" vector, and the like.

A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like), and includes both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

Host Cells and Transformed Cells

The invention also provides a transformed cell comprising a nucleic acid sequence of the invention, e.g., a sequence encoding a polypeptide of the invention, or a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces*, and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation.

Engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

Amplification of Nucleic Acids

In practicing the invention, nucleic acids encoding the polypeptides of the invention, or modified nucleic acids, can be reproduced by, e.g., amplification. The invention provides amplification primer sequence pairs for amplifying nucleic acids encoding polypeptides of the invention, e.g., primer pairs capable of amplifying nucleic acid sequences comprising the exemplary SEQ ID NO:1, or subsequences thereof.

Amplification methods include, e.g., polymerase chain reaction, PCR (PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR); transcription amplification and other RNA polymerase mediated techniques (e.g., NASBA, Cangene, Mississauga, Ontario); see also Sambrook; Ausubel.

Hybridization of Nucleic Acids

The invention provides isolated or recombinant nucleic acids that hybridize under stringent conditions to an exemplary sequence of the invention, e.g., a sequence as set forth in SEQ ID NO:1, or the complement of any thereof, or a nucleic acid that encodes a polypeptide of the invention. In alternative aspects, the stringent conditions are highly stringent conditions, medium stringent conditions or low stringent conditions, as known in the art and as described herein. These methods may be used to isolate nucleic acids of the invention.

In alternative aspects, nucleic acids of the invention as defined by their ability to hybridize under stringent conditions can be between about five residues and the full length of nucleic acid of the invention; e.g., they can be at least 5, 10, 15, 20, 25, 30, 35, 40, 50, 55, 60, 65, 70, 75, 80, 90, 100, 150, 200, 250 or more residues in length, or, the full length of a gene or coding sequence, e.g., cDNA. Nucleic acids shorter than full length are also included. These nucleic acids can be useful as, e.g., hybridization probes, labeling probes, PCR oligonucleotide probes, iRNA, antisense or sequences encoding antibody binding peptides (epitopes), motifs, active sites and the like.

"Hybridization" refers to the process by which a nucleic acid strand joins with a complementary strand through base pairing. Hybridization reactions can be sensitive and selective so that a particular sequence of interest can be identified even in samples in which it is present at low concentrations. Stringent conditions can be defined by, for example, the concentrations of salt or formamide in the prehybridization and hybridization solutions, or by the hybridization temperature, and are well known in the art. For example, stringency can be increased by reducing the concentration of salt, increasing the concentration of formamide, or raising the hybridization temperature, altering the time of hybridization, as described in detail, below. In alternative aspects, nucleic acids of the invention are defined by their ability to hybridize under various stringency conditions (e.g., high, medium, and low), as set forth herein.

In one aspect, nucleic acids of the invention are defined by their ability to hybridize under high stringency comprises conditions of about 50% formamide at about 37° C. to 42° C. In one aspect, nucleic acids of the invention are defined by their ability to hybridize under reduced stringency comprising conditions in about 35% to 25% formamide at about 30° C. to 35° C. Alternatively, nucleic acids of the invention are defined by their ability to hybridize under high stringency comprising conditions at 42° C. in 50% formamide, 5×SSPE, 0.3% SDS, and a repetitive sequence blocking nucleic acid, such as cot-1 or salmon sperm DNA (e.g., 200 ng/ml sheared and denatured salmon sperm DNA). In one aspect, nucleic acids of the invention are defined by their ability to hybridize under reduced stringency conditions comprising 35% formamide at a reduced temperature of 35° C.

Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

The temperature range corresponding to a particular level of stringency can be further narrowed by calculating the purine to pyrimidine ratio of the nucleic acid of interest and adjusting the temperature accordingly. Nucleic acids of the invention are also defined by their ability to hybridize under high, medium, and low stringency conditions as set forth in Ausubel and Sambrook. Variations on the above ranges and conditions are well known in the art.

Oligonucleotides Probes and Methods for using them

The invention also provides nucleic acid probes for identifying nucleic acids encoding a polypeptide with an NFκB-inhibiting activity. In one aspect, the probe comprises at least 10 consecutive bases of a nucleic acid of the invention. Alternatively, a probe of the invention can be at least about 5, 6, 7, 8, 9, 10, 15, 20, 25, 30, 35, 40, 45, 50, 60, 70, 80, 90, 100, 110, 120, 130, 150, 200, 250, 300 or about 10 to 50, about 20 to 60 about 30 to 70, consecutive bases of a sequence as set forth in a nucleic acid of the invention. The probes identify a nucleic acid by binding and/or hybridization. The probes can be used in arrays of the invention. The probes of the invention can also be used to isolate other nucleic acids or polypeptides.

Determining the Degree of Sequence Identity

The invention provides nucleic acids having at least 90%, 91%, 92%, 93%, 94%, 95%, 96%, 97%, 98%, 99% or more sequence identity to SEQ ID NO:1. The invention provides polypeptides having at least 90%, 91%, 92%, 93%, 94%, 95%, 96%, 97%, 98%, 99% or more sequence identity to SEQ ID NO:2. The sequence identities can be determined by analysis with a sequence comparison algorithm or by a visual inspection.

Protein and/or nucleic acid sequence identities (homologies) may be evaluated using any of the variety of sequence comparison algorithms and programs known in the art. The extent of sequence identity (homology) may be determined using any computer program and associated parameters, such as those described in US 2004/0072228 A1, such as BLAST 2.2.2. or FASTA version 3.0t78, with the default parameters.

The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. For sequence comparison, one sequence can act as a reference sequence (an exemplary sequence SEQ ID NO:1, SEQ ID NO:2) to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the numbers of contiguous residues. For example, in alternative aspects of the invention, continuous residues ranging anywhere from 20 to the full length of an exemplary polypeptide or nucleic acid sequence of the invention, e.g., SEQ ID NO:1, SEQ ID NO:2, are compared to a reference sequence of the same number of contiguous positions after the two sequences are optimally aligned. If the reference sequence has the requisite sequence identity to an exemplary polypeptide or nucleic acid sequence of the invention, e.g., at least 90%, 91%, 92%, 93%, 94%, 95%, 96%, 97%, 98%, 99% or more sequence identity to SEQ ID NO:1, SEQ ID NO:2, that sequence is within the scope of the invention.

The phrase "substantially identical" in the context of two nucleic acids or polypeptides, can refer to two or more sequences that have, e.g., at least about at least 90%, 91%, 92%, 93%, 94%, 95%, 96%, 97%, 98%, 99% or more sequence identity or more nucleotide or amino acid residue (sequence) identity, when compared and aligned for maximum correspondence, as measured using one any known sequence comparison algorithm, as discussed in detail below, or by visual inspection. In alternative aspects, the invention provides nucleic acid and polypeptide sequences having substantial identity to an exemplary sequence of the invention, e.g., SEQ ID NO:1, SEQ ID NO:2, over a region of at least about 10, 20, 30, 40, 50 or more residues, or a region ranging from between about 50 residues to the full length of the nucleic acid or polypeptide. Nucleic acid sequences of the invention can be substantially identical over the entire length of a polypeptide coding region.

Inhibiting Expression of Polypeptides and Transcripts

The invention further provides for nucleic acids complementary to (e.g., antisense sequences to) the nucleic acid sequences of the invention. Antisense sequences are capable of inhibiting the transport, splicing or transcription of protein-encoding genes, e.g., the POP2 polypeptide encoding nucleic acids of the invention. The inhibition can be effected through the targeting of genomic DNA or messenger RNA. The transcription or function of targeted nucleic acid can be inhibited, for example, by hybridization and/or cleavage. One particularly useful set of inhibitors provided by the present invention includes oligonucleotides which are able to either bind gene or message, in either case preventing or inhibiting the production or function of the protein. The association can be through sequence specific hybridization. Another useful class of inhibitors includes oligonucleotides which cause inactivation or cleavage of protein message. The oligonucleotide can have enzyme activity which causes such cleavage, such as ribozymes. The oligonucleotide can be chemically modified or conjugated to an enzyme or composition capable of cleaving the complementary nucleic acid. One may screen a pool of many different such oligonucleotides for those with the desired activity.

General methods of using antisense, ribozyme technology and RNAi technology, to control gene expression, or of gene therapy methods for expression of an exogenous gene in this manner are well known in the art. Each of these methods utilizes a system, such as a vector, encoding either an antisense or ribozyme transcript of a phosphatase polypeptide of the invention. The term "RNAi" stands for RNA interference. This term is understood in the art to encompass technology using RNA molecules that can silence genes. The term "RNAi" encompasses molecules such as short interfering RNA (siRNA), microRNAs (mRNA), small temporal RNA (stRNA). Generally speaking, RNA interference results from the interaction of double-stranded RNA with genes.

Antisense Oligonucleotides

The invention provides antisense oligonucleotides capable of binding polypeptide messages which can inhibit polypeptide activity by targeting mRNA. Strategies for designing antisense oligonucleotides are well described in the scientific and patent literature, and the skilled artisan can design such oligonucleotides using the novel reagents of the invention. For example, gene walking/RNA mapping protocols to screen for effective antisense oligonucleotides are well known in the art, see, e.g., Ho (2000) Methods Enzymol. 314:168-183, describing an RNA mapping assay, which is based on standard molecular techniques to provide an easy and reliable method for potent antisense sequence selection. See also Smith (2000) Eur. J. Pharm. Sci. 11:191-198.

Naturally occurring nucleic acids are used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. Combinatorial chemistry methodology can be used to create vast numbers of oligonucleotides that can be rapidly screened for specific oligonucleotides that have appropriate binding affinities and specificities toward any target, such as the sense and antisense polypeptides sequences of the invention.

siRNA

"Small interfering RNA" (siRNA) refers to double-stranded RNA molecules from about 10 to about 30 nucleotides long that are named for their ability to specifically interfere with protein expression through RNA interference (RNAi). Preferably, siRNA molecules are 12-28 nucleotides long, more preferably 15-25 nucleotides long, still more preferably 19-23 nucleotides long and most preferably 21-23 nucleotides long. Therefore, preferred siRNA molecules are 12, 13, 14, 15, 16, 17, 18, 19, 20, 21, 22, 23, 24, 25, 26, 27 28 or 29 nucleotides in length.

RNAi is a two step mechanism. First, long dsRNAs are cleaved by an enzyme known as Dicer into 21-23 ribonucleotide (nt) fragments, called small interfering RNAs (siRNAs). Then, siRNAs associate with a ribonuclease complex (termed RISC for RNA Induced Silencing Complex) which target this complex to complementary mRNAs. RISC then cleaves the targeted mRNAs opposite the complementary siRNA, which makes the mRNA susceptible to other RNA degradation pathways.

siRNAs of the present invention are designed to interact with a target ribonucleotide sequence, meaning they complement a target sequence sufficiently to bind to the target sequence. The present invention also includes siRNA molecules that have been chemically modified to confer increased stability against nuclease degradation, but retain the ability to bind to target nucleic acids that may be present.

Inhibitory Ribozymes

The invention provides ribozymes capable of binding message which can inhibit polypeptide activity by targeting mRNA, e.g., inhibition of polypeptides with POP2 activity, e.g., NFκB inhibiting activity. Strategies for designing ribozymes and selecting the protein-specific antisense sequence for targeting are well described in the scientific and patent literature, and the skilled artisan can design such ribozymes using the novel reagents of the invention.

Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it is typically released from that RNA and so can bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site.

The enzymatic ribozyme RNA molecule can be formed in a hammerhead motif, but may also be formed in the motif of a hairpin, hepatitis delta virus, group I intron or RNaseP-like RNA (in association with an RNA guide sequence). The recitation of these specific motifs is not intended to be limiting; those skilled in the art will recognize that an enzymatic RNA molecule of this invention has a specific substrate binding site complementary to one or more of the target gene RNA regions, and has nucleotide sequence within or surrounding that substrate binding site which imparts an RNA cleaving activity to the molecule.

Peptides and Polypeptides

The invention provides isolated or recombinant polypeptides comprising an amino acid sequence having at least 95%, 96%, 97%, 98%, 99% or more sequence identity to SEQ ID NO:2 over a region of at least about 40, 50, 60, 70, 80, 90 or more residues, or, the full length of the polypeptide, or, a polypeptide encoded by a nucleic acid of the invention. In one aspect, the polypeptide comprises a sequence as set forth in SEQ ID NO:2. The invention provides methods for inhibiting the activity of a POP2 polypeptide, e.g., a polypeptide of the invention. The invention also provides methods for screening for compositions that inhibit the activity of, or bind to (e.g., bind to the active site), of a POP2 polypeptide, e.g., a polypeptide of the invention.

The peptides and polypeptides of the invention can be expressed recombinantly in vivo after administration of nucleic acids, as described above, or, they can be administered directly, e.g., as a pharmaceutical composition. They can be expressed in vitro or in vivo to screen for modulators of a POP2 activity.

Polypeptides and peptides of the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. For example, peptide synthesis can be performed using various solid-phase techniques and automated synthesis may be achieved, e.g., using the ABI 431A Peptide Synthesizer (Perkin Elmer) in accordance with the instructions provided by the manufacturer.

The invention also provides polypeptides that are "substantially identical" to an exemplary polypeptide of the invention. A "substantially identical" amino acid sequence is a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from a POP2 polypeptide of the invention, resulting in modification of the structure of the polypeptide, without significantly altering its biological activity. For example, amino- or carboxyl-terminal, or internal, amino acids which are not required for NFκB inhibiting activity can be removed.

The skilled artisan will recognize that individual synthetic residues and polypeptides incorporating these mimetics can be synthesized using a variety of procedures and methodologies, which are well described in the scientific and patent literature, e.g., Organic Syntheses Collective Volumes, Gilman, et al. (Eds) John Wiley & Sons, Inc., NY. Peptides and peptide mimetics of the invention can also be synthesized using combinatorial methodologies. Various techniques for generation of peptide and peptidomimetic libraries are well known, and include, e.g., multipin, tea bag, and split-couple-mix techniques; see, e.g., al-Obeidi (1998) Mol. Biotechnol. 9:205-223; Hruby (1997) Curr. Opin. Chem. Biol. 1:114-119; Ostergaard (1997) Mol. Divers. 3:17-27; Ostresh (1996) Methods Enzymol. 267:220-234. Modified peptides of the invention can be further produced by chemical modification methods, see, e.g., Belousov (1997) Nucleic Acids Res. 25:3440-3444; Frenkel (1995) Free Radic. Biol. Med. 19:373-380; Blommers (1994) Biochemistry 33:7886-7896.

Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Technology pertaining to vectors encoding fusion proteins and application of fusion proteins are well described in the scientific and patent literature, see e.g., Kroll (1993) DNA Cell. Biol., 12:441-53.

The terms "polypeptide" and "protein" as used herein, refer to amino acids joined to each other by peptide bonds. The term "polypeptide" also includes peptides and polypeptide fragments, motifs and the like. The term also includes glycosylated polypeptides. The peptides and polypeptides of the invention also include all "mimetic" and "peptidomimetic" forms.

As used herein, the term "isolated" means that the material is removed from its original environment (e.g., the natural environment if it is naturally occurring). For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment. As used herein, an isolated material or composition can also be a "purified" composition or "substantially pure", i.e., it does not require absolute purity; rather, it is intended as a relative definition. Individual nucleic acids obtained from a library can be conventionally purified to electrophoretic homogeneity. In alternative aspects, the invention provides nucleic acids which have been purified from genomic DNA or from other sequences in a library or other environment by at least one, two, three, four, five or more orders of magnitude.

An exemplary POP2 is presented below; SEQ ID NO:1 being the nucleic acid sequence, and SEQ ID NO:2 being the amino acid translation thereof:

```
atg gca tct tct gca gag ctg gac ttc      SEQ ID NO. 1
aac ctg cag gct ctt ctg gag cag ctc
agc cag gat gag ttg agc aag ttc aag
tct ctg atc aga aca atc tcc ctg gga
aag gag cta cag acc gtc ccc cag aca
gag gta gac aag gct aat ggg aag caa
ctg gta gaa atc ttc acc agc cac tcc
tgc agc tac tgg gca ggg atg gca gcc
atc cag gtc ttt gaa aag atg aat caa
acg cat ctg tct ggg aga gct gat gaa
cac tgt gtg atg ccc cca cct taa
```

```
MAS SAE LDF NLQ ALL EQL SQD ELS KFK      SEQ ID NO. 2
SLI RTI SLG KEL QTV PQT EVD KAN GKQ
LVE IFT SHS CSY WAG MAA IQV FEK MNQ
THL SGR ADE HCV MPP P*
```

Screening Methodologies

In practicing the methods of the invention, a variety of apparatus and methodologies can be used to in conjunction with the polypeptides and nucleic acids of the invention, e.g., to screen polypeptides for NFκB inhibiting activity, to screen compounds as potential modulators (e.g., inhibitors or activators) of a POP2 activity, e.g., an NFκB inhibiting activity, for antibodies that bind to a polypeptide of the invention, for nucleic acids that hybridize to a nucleic acid of the invention, to screen for cells expressing a polypeptide of the invention and the like.

In one aspect, the peptides and polypeptides of the invention can be bound to a solid support. Solid supports can include, e.g., membranes (e.g., nitrocellulose or nylon), a microtiter dish (e.g., PVC, polypropylene, or polystyrene), a test tube (glass or plastic), a dip stick (e.g., glass, PVC, polypropylene, polystyrene, latex and the like), a microfuge tube, or a glass, silica, plastic, metallic or polymer bead or other substrate such as paper. One solid support uses a metal (e.g., cobalt or nickel)-comprising column which binds with specificity to a histidine tag engineered onto a peptide.

Adhesion of peptides to a solid support can be direct (i.e., the protein contacts the solid support) or indirect (a particular compound or compounds are bound to the support and the target protein binds to this compound rather than the solid support). Peptides can be immobilized either covalently (e.g., utilizing single reactive thiol groups of cysteine residues (see, e.g., Colliuod (1993) Bioconjugate Chem. 4:528-536) or non-covalently but specifically (e.g., via immobilized antibodies (see, e.g., Schuhmann (1991) Adv. Mater. 3:388-391; Lu (1995) Anal. Chem. 67:83-87; the biotin/strepavidin system (see, e.g., Iwane (1997) Biophys. Biochem. Res. Comm. 230: 76-80); metal chelating, e.g., Langmuir-Blodgett films (see, e.g., Ng (1995) Langmuir 11:4048-55); metal-chelating self-assembled monolayers (see, e.g., Sigal (1996) Anal. Chem. 68:490-497) for binding of polyhistidine fusions.

Indirect binding can be achieved using a variety of linkers which are commercially available. The reactive ends can be any of a variety of functionalities including, but not limited to:

amino reacting ends such as N-hydroxysuccinimide (NHS) active esters, imidoesters, aldehydes, epoxides, sulfonyl halides, isocyanate, isothiocyanate, and nitroaryl halides; and thiol reacting ends such as pyridyl disulfides, maleimides, thiophthalimides, and active halogens. The heterobifunctional crosslinking reagents have two different reactive ends, e.g., an amino-reactive end and a thiol-reactive end, while homobifunctional reagents have two similar reactive ends, e.g., bismaleimidohexane (BMH) which permits the cross-linking of sulfhydryl-containing compounds. The spacer can be of varying length and be aliphatic or aromatic. Examples of commercially available homobifunctional cross-linking reagents include, but are not limited to, the imidoesters such as dimethyl adipimidate dihydrochloride (DMA); dimethyl pimelimidate dihydrochloride (DMP); and dimethyl suberimidate dihydrochloride (DMS). Heterobifunctional reagents include commercially available active halogen-NHS active esters coupling agents such as N-succinimidyl bromoacetate and N-succinimidyl (4-iodoacetyl)aminobenzoate (SLAB) and the sulfosuccinimidyl derivatives such as sulfosuccinimidyl(4-iodoacetyl)aminobenzoate (sulfo-SIAB) (Pierce). Another group of coupling agents is the heterobifunctional and thiol cleavable agents such as N-succinimidyl 3-(2-pyridyidithio)propionate (SPDP) (Pierce Chemicals, Rockford, Ill.).

Antibodies can be used for binding polypeptides and peptides of the invention to a solid support. This can be done directly by binding peptide-specific antibodies to the column or it can be done by creating fusion protein chimeras comprising motif-containing peptides linked to, e.g., a known epitope (e.g., a tag (e.g., FLAG, myc) or an appropriate immunoglobulin constant domain sequence (an "immunoadhesin," see, e.g., Capon (1989) Nature 377:525-531 (1989).

Arrays or "Biochips"

The invention provides methods for identifying/screening for modulators (e.g., inhibitors, activators) of a POP2 activity, e.g., an NFκB inhibiting activity, using arrays. Potential modulators, including small molecules, nucleic acids, polypeptides (including antibodies) can be immobilized to arrays. Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention, e.g., a POP2 activity. For example, in one aspect of the invention, a monitored parameter is transcript expression of a gene comprising a nucleic acid of the invention. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. Polypeptide arrays can be used to simultaneously quantify a plurality of proteins. Small molecule arrays can be used to simultaneously analyze a plurality of POP2 modulating or binding activities.

The present invention can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts. The terms "array" or "microarray" or "biochip" or "chip" as used herein is a plurality of target elements, each target element comprising a defined amount of one or more polypeptides (including antibodies) or nucleic acids immobilized onto a defined area of a substrate surface.

Antibodies and Antibody-Based Screening Methods

The invention provides isolated or recombinant antibodies that specifically bind to a polypeptide or nucleic acid of the invention. These antibodies can be used to isolate, identify or quantify a polypeptide of the invention or related polypeptides. These antibodies can be used to isolate other polypeptides within the scope the invention or other related NFκB inhibiting polypeptides.

The term "antibody" includes a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

The antibodies can be used in immunoprecipitation, staining (e.g., FACS), immunoaffinity columns, and the like. If desired, nucleic acid sequences encoding for specific antigens can be generated by immunization followed by isolation of polypeptide or nucleic acid, amplification or cloning and immobilization of polypeptide onto an array of the invention. Alternatively, the methods of the invention can be used to modify the structure of an antibody produced by a cell to be modified, e.g., an antibody's affinity can be increased or decreased. Furthermore, the ability to make or modify antibodies can be a phenotype engineered into a cell by the methods of the invention.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu. Rev. Biophys. Biomol. Struct. 26:27-45.

Polypeptides or peptides can be used to generate antibodies which bind specifically to the polypeptides of the invention.

The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the invention.

In immunoaffinity procedures, the antibody is attached to a solid support, such as a bead or other column matrix. The protein preparation is placed in contact with the antibody under conditions in which the antibody specifically binds to one of the polypeptides of the invention. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of the invention can be obtained by direct injection of the polypeptides into an animal or by administering the polypeptides to a non-human animal. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique, the trioma technique, the human B-cell hybridoma technique, and the EBV-hybridoma technique (see, e.g., Cole (1985) in Monoclonal Antibodies and Cancer Therapy, Alan R. Liss, Inc., pp. 77-96).

Techniques described for the production of single chain antibodies (see, e.g., U.S. Pat. No. 4,946,778) can be adapted to produce single chain antibodies to the polypeptides of the invention. Alternatively, transgenic mice may be used to express humanized antibodies to these polypeptides or fragments thereof.

Antibodies generated against the polypeptides of the invention may be used in screening for similar polypeptides from other organisms and samples. In such techniques, polypeptides from the organism are contacted with the antibody and those polypeptides which specifically bind the antibody are detected. Any of the procedures described above may be used to detect antibody binding.

Therapeutic Applications

The compounds and modulators identified by the methods of the present invention may be used in a variety of methods of treatment. Thus, the present invention provides compositions and methods for treating an autoimmune disease or disorder or a lymphoma broad spectrum of diseases associated with sustained NF-κB activity including Alzheimer's, autoimmune diseases, and cancer.

Exemplary autoimmune diseases are acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcalnephritis, erythema nodosurn, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitisubiterans, Sjogren's syndrome, primary biliary cirrhosis, Hashimoto's thyroiditis, thyrotoxicosis, scleroderma, chronic active hepatitis, polymyositis/dermatomyositis, polychondritis, parnphigus vulgaris, Wegener's granulomatosis, membranous nephropathy, amyotrophic lateral sclerosis, tabes dorsalis, giant cell arteritis/polymyalgia, pemiciousanemia, rapidly progressive glomerulonephritis and fibrosing alveolitis.

Formulation and Administration of Pharmaceutical Compositions

The invention provides pharmaceutical compositions comprising nucleic acids, peptides and polypeptides (including Abs) of the invention. As discussed above, the nucleic acids, peptides and polypeptides of the invention can be used to inhibit or activate expression of an endogenous POP2 polypeptide.

The nucleic acids, peptides and polypeptides of the invention can be combined with a pharmaceutically acceptable carrier (excipient) to form a pharmacological composition. Pharmaceutically acceptable carriers can contain a physiologically acceptable compound that acts to, e.g., stabilize, or increase or decrease the absorption or clearance rates of the pharmaceutical compositions of the invention. Physiologically acceptable compounds can include, e.g., carbohydrates, such as glucose, sucrose, or dextrans, antioxidants, such as ascorbic acid or glutathione, chelating agents, low molecular weight proteins, compositions that reduce the clearance or hydrolysis of the peptides or polypeptides, or excipients or other stabilizers and/or buffers. Detergents can also used to stabilize or to increase or decrease the absorption of the pharmaceutical composition, including liposomal carriers. Pharmaceutically acceptable carriers and formulations for peptides and polypeptide are known to the skilled artisan and are described in detail in the scientific and patent literature, see e.g., the latest edition of Remington's Pharmaceutical Science, Mack Publishing Company, Easton, Pa. ("Remington's").

Other physiologically acceptable compounds include wetting agents, emulsifying agents, dispersing agents or preservatives which are particularly useful for preventing the growth or action of microorganisms. Various preservatives are well known and include, e.g., phenol and ascorbic acid. One skilled in the art would appreciate that the choice of a pharmaceutically acceptable carrier including a physiologically acceptable compound depends, for example, on the route of administration of the peptide or polypeptide of the invention and on its particular physio-chemical characteristics.

In one aspect, a solution of nucleic acids, peptides or polypeptides of the invention are dissolved in a pharmaceutically acceptable carrier, e.g., an aqueous carrier if the composition is water-soluble. Examples of aqueous solutions that can be used in formulations for enteral, parenteral or transmucosal drug delivery include, e.g., water, saline, phosphate buffered saline, Hank's solution, Ringer's solution, dextrose/saline, glucose solutions and the like. The formulations can contain pharmaceutically acceptable auxiliary substances as required to approximate physiological conditions, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. These compositions can be sterilized by conventional, well-known sterilization techniques, or can be sterile filtered. The resulting aqueous solutions can be packaged for use as is, or lyophilized, the lyophilized preparation being combined with a sterile aqueous solution prior to administration. The concentration of peptide in these formulations can vary widely, and will be selected primarily based on fluid volumes, viscosities, body weight and the like in accordance with the particular mode of administration selected and the patient's needs.

Solid formulations can be used for enteral (oral) administration. They can be formulated as, e.g., pills, tablets, powders or capsules. For solid compositions, conventional nontoxic solid carriers can be used which include, e.g., pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10% to 95% of active ingredient (e.g., peptide). A non-solid formulation can also be used for enteral administration. The carrier can be selected from various oils including those of petroleum, animal, vegetable or synthetic origin, e.g., peanut oil, soybean oil, mineral oil, sesame oil, and the like. Suitable pharmaceutical excipients include e.g., starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol.

Nucleic acids, peptides or polypeptides of the invention, when administered orally, can be protected from digestion. This can be accomplished either by complexing the nucleic acid, peptide or polypeptide with a composition to render it resistant to acidic and enzymatic hydrolysis or by packaging the nucleic acid, peptide or polypeptide in an appropriately resistant carrier such as a liposome. Means of protecting compounds from digestion are well known in the art, see, e.g., Fix (1996) Pharm Res. 13:1760-1764; Samanen (1996) J. Pharm. Pharmacol. 48:119-135; U.S. Pat. No. 5,391,377, describing lipid compositions for oral delivery of therapeutic agents (liposomal delivery is discussed in further detail, infra).

Systemic administration can also be by transmucosal or transdermal means. For transmucosal or transdermal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays or using suppositories. See, e.g., Sayani (1996) "Systemic delivery of peptides and proteins across absorptive mucosae" Crit. Rev. Ther. Drug Carrier Syst. 13:85-184. For topical, transdermal administration, the agents are formulated into ointments, creams, salves, powders and gels. Transdermal delivery systems can also include, e.g., patches.

The nucleic acids, peptides or polypeptides of the invention can also be administered in sustained delivery or sustained release mechanisms, which can deliver the formulation internally. For example, biodegradeable microspheres or capsules or other biodegradeable polymer configurations capable of sustained delivery of a peptide can be included in the formulations of the invention (see, e.g., Putney (1998) Nat. Biotechnol. 16:153-157).

For inhalation, the nucleic acids, peptides or polypeptides of the invention can be delivered using any system known in the art, including dry powder aerosols, liquids delivery systems, air jet nebulizers, propellant systems, and the like. See, e.g., Patton (1998) Biotechniques 16:141-143; product and inhalation delivery systems for polypeptide macromolecules by, e.g., Dura Pharmaceuticals (San Diego, Calif.), Aradigm (Hayward, Calif.), Aerogen (Santa Clara, Calif.), Inhale Therapeutic Systems (San Carlos, Calif.), and the like. For example, the pharmaceutical formulation can be administered in the form of an aerosol or mist. For aerosol administration, the formulation can be supplied in finely divided form along with a surfactant and propellant. In another aspect, the device for delivering the formulation to respiratory tissue is an inhaler in which the formulation vaporizes. Other liquid delivery systems include, e.g., air jet nebulizers.

In preparing pharmaceuticals of the present invention, a variety of formulation modifications can be used and manipulated to alter pharmacokinetics and biodistribution. A number of methods for altering pharmacokinetics and biodistribution are known to one of ordinary skill in the art. Examples of such methods include protection of the compositions of the invention in vesicles composed of substances such as proteins, lipids (for example, liposomes), carbohydrates, or synthetic polymers (discussed above). For a general discussion of pharmacokinetics, see, e.g., Remington's, Chapters 37-39.

Treatment Regimens: Pharmacokinetics

The pharmaceutical compositions of the invention can be administered in a variety of unit dosage forms depending upon the method of administration. Dosages for typical nucleic acid, peptide and polypeptide pharmaceutical compositions are well known to those of skill in the art. Such dosages are typically advisorial in nature and are adjusted depending on the particular therapeutic context, patient tolerance, etc. The amount of nucleic acid, peptide or polypeptide adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age, pharmaceutical formulation and concentration of active agent, and the like. In calculating the dosage regimen for a patient, the mode of administration also is taken into consideration. The dosage regimen must also take into consideration the pharmacokinetics, i.e., the pharmaceutical composition's rate of absorption, bioavailability, metabolism, clearance, and the like.

While the invention has been described and exemplified in sufficient detail for those skilled in this art to make and use it, various alternatives, modifications, and improvements should be apparent without departing from the spirit and scope of the invention. The present invention is well adapted to carry out the objects and obtain the ends and advantages mentioned, as well as those inherent therein. The examples provided here are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

The disclosure of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method for inhibiting NFκB activity in a cell comprising directly administering to the cell a vector comprised of a cDNA having a sequence consisting of SEQ ID NO:1 wherein the cDNA is operatively linked to a promotor.

* * * * *

```
                        SEQUENCE LISTING

<160> NUMBER OF SEQ ID NOS: 28

<210> SEQ ID NO 1
<211> LENGTH: 294
<212> TYPE: DNA
<213> ORGANISM: Homo sapiens

<400> SEQUENCE: 1
atggcatctt ctgcagagct ggacttcaac ctgcaggctc ttctggagca gctcagccag      60
gatgagttga gcaagttcaa gtctctgatc agaacaatct ccctgggaaa ggagctacag     120
accgtccccc agacagaggt agacaaggct aatgggaagc aactggtaga aatcttcacc     180
agccactcct gcagctactg gcagggatg gcagccatcc aggtctttga aaagatgaat      240
caaacgcatc tgtctgggag agctgatgaa cactgtgtga tgccccacc ttaa            294

<210> SEQ ID NO 2
<211> LENGTH: 97
<212> TYPE: PRT
<213> ORGANISM: Homo sapiens

<400> SEQUENCE: 2

Met Ala Ser Ser Ala Glu Leu Asp Phe Asn Leu Gln Ala Leu Leu Glu
1               5                  10                  15

Gln Leu Ser Gln Asp Glu Leu Ser Lys Phe Lys Ser Leu Ile Arg Thr
            20                  25                  30

Ile Ser Leu Gly Lys Glu Leu Gln Thr Val Pro Gln Thr Glu Val Asp
        35                  40                  45

Lys Ala Asn Gly Lys Gln Leu Val Glu Ile Phe Thr Ser His Ser Cys
    50                  55                  60

Ser Tyr Trp Ala Gly Met Ala Ala Ile Gln Val Phe Glu Lys Met Asn
65                  70                  75                  80

Gln Thr His Leu Ser Gly Arg Ala Asp Glu His Cys Val Met Pro Pro
                85                  90                  95

Pro

<210> SEQ ID NO 3
<211> LENGTH: 26
<212> TYPE: DNA
<213> ORGANISM: artificial
<220> FEATURE:
<223> OTHER INFORMATION: Forward amplification primer

<400> SEQUENCE: 3
aaccgcggat ggcatcttct gcagag                                          26

<210> SEQ ID NO 4
<211> LENGTH: 26
<212> TYPE: DNA
<213> ORGANISM: artificial
<220> FEATURE:
<223> OTHER INFORMATION: Reverse amplification primer

<400> SEQUENCE: 4
aaaagcttat ggcatcttct gcagag                                          26
```

<210> SEQ ID NO 5
<211> LENGTH: 457
<212> TYPE: DNA
<213> ORGANISM: Homo sapiens

<400> SEQUENCE: 5

```
atggcatctt ctgcagagct ggacttcaac ctgcaggctc ttctggagca gctcagccag      60
gatgagttga gcaagttcaa gtctctgatc agaacaatct ccctgggaaa ggagctacag     120
accgtccccc agacagaggt agacaaggct aatgggaagc aactggtaga aatcttcacc     180
agccactcct gcagctactg ggcagggatg cagccatcc aggtctttga aaagatgaat      240
caaacgcatc tgtctgggag agctgatgaa cactgtgtga tgccccacc ttaaccccctc     300
agggatagtg agttgatggc tgagctagat gttgctttag ccttggttct gtctccatt     360
tacatgcaca tgttgcttaa ccttgttata tatgaaatat ctaatatcac cagtattttg     420
agataaataa aggtgaaata attcacaaac attaaaa                              457
```

<210> SEQ ID NO 6
<211> LENGTH: 100
<212> TYPE: PRT
<213> ORGANISM: Homo sapiens

<400> SEQUENCE: 6

```
Met Val Ser Ser Ala Gln Met Gly Phe Asn Leu Gln Ala Leu Leu Glu
1               5                   10                  15

Gln Leu Ser Gln Asp Glu Leu Ser Lys Phe Lys Tyr Leu Ile Thr Thr
            20                  25                  30

Phe Ser Leu Ala His Glu Leu Gln Lys Ile Pro His Lys Glu Val Asp
        35                  40                  45

Lys Ala Asp Gly Lys Gln Leu Val Glu Ile Leu Thr Thr His Cys Asp
    50                  55                  60

Ser Tyr Trp Val Glu Met Ala Ser Leu Gln Val Phe Glu Lys Met His
65                  70                  75                  80

Arg Met Asp Leu Ser Glu Arg Ala Lys Asp Glu Val Arg Glu Ala Ala
                85                  90                  95

Leu Lys Ser Phe
            100
```

<210> SEQ ID NO 7
<211> LENGTH: 100
<212> TYPE: PRT
<213> ORGANISM: Homo sapiens

<400> SEQUENCE: 7

```
Met Thr Ser Pro Gln Leu Glu Trp Thr Leu Gln Thr Leu Leu Glu Gln
1               5                   10                  15

Leu Asn Glu Asp Glu Leu Lys Ser Phe Lys Ser Leu Leu Trp Ala Phe
            20                  25                  30

Pro Leu Glu Asp Val Leu Gln Lys Thr Pro Trp Ser Glu Val Glu Glu
        35                  40                  45

Ala Asp Gly Lys Lys Leu Ala Glu Ile Leu Val Asn Thr Ser Ser Glu
    50                  55                  60

Asn Trp Ile Arg Asn Ala Thr Val Asn Ile Leu Glu Glu Met Asn Leu
65                  70                  75                  80
```

Thr Glu Leu Cys Lys Met Ala Lys Ala Glu Met Met Glu Asp Gly Gln
                85                  90                  95

Val Gln Glu Ile
            100

<210> SEQ ID NO 8
<211> LENGTH: 100
<212> TYPE: PRT
<213> ORGANISM: Homo sapiens

<400> SEQUENCE: 8

Met Ala Ala Ser Phe Phe Ser Asp Phe Gly Leu Met Trp Tyr Leu Glu
1               5                   10                  15

Glu Leu Lys Lys Glu Glu Phe Arg Lys Phe Lys Glu His Leu Lys Gln
            20                  25                  30

Met Thr Leu Gln Leu Glu Leu Lys Gln Ile Pro Trp Thr Glu Val Lys
        35                  40                  45

Lys Ala Ser Arg Glu Glu Leu Ala Asn Leu Leu Ile Lys His Tyr Glu
    50                  55                  60

Glu Gln Gln Ala Trp Asn Ile Thr Leu Arg Ile Phe Gln Lys Met Asp
65                  70                  75                  80

Arg Lys Asp Leu Cys Met Lys Val Met Arg Glu Arg Thr Gly Tyr Thr
                85                  90                  95

Lys Thr Tyr Gln
            100

<210> SEQ ID NO 9
<211> LENGTH: 100
<212> TYPE: PRT
<213> ORGANISM: Homo sapiens

<400> SEQUENCE: 9

Met Ala Glu Ser Phe Phe Ser Asp Phe Gly Leu Leu Trp Tyr Leu Lys
1               5                   10                  15

Glu Leu Arg Lys Glu Glu Phe Trp Lys Phe Lys Glu Leu Leu Lys Gln
            20                  25                  30

Pro Leu Glu Lys Phe Glu Leu Lys Pro Ile Pro Trp Ala Glu Leu Lys
        35                  40                  45

Lys Ala Ser Lys Glu Asp Val Ala Lys Leu Leu Asp Lys His Tyr Pro
    50                  55                  60

Gly Lys Gln Ala Trp Glu Val Thr Leu Asn Leu Phe Leu Gln Ile Asn
65                  70                  75                  80

Arg Lys Asp Leu Trp Thr Lys Ala Gln Glu Glu Met Arg Asn Lys Leu
                85                  90                  95

Asn Pro Tyr Arg
            100

<210> SEQ ID NO 10
<211> LENGTH: 100
<212> TYPE: PRT
<213> ORGANISM: Homo sapiens

<400> SEQUENCE: 10

Met Ala Glu Ser Asp Ser Thr Asp Phe Asp Leu Leu Trp Tyr Leu Glu
1               5                   10                  15

Asn Leu Ser Asp Lys Glu Phe Gln Ser Phe Lys Lys Tyr Leu Ala Arg
            20                  25                  30

-continued

Lys Ile Leu Asp Phe Lys Leu Pro Gln Phe Pro Leu Ile Gln Met Thr
            35                  40                  45

Lys Glu Glu Leu Ala Asn Val Leu Pro Ile Ser Tyr Glu Gly Gln Tyr
 50                      55                  60

Ile Trp Asn Met Leu Phe Ser Ile Phe Ser Met Met Arg Lys Glu Asp
 65                  70                  75                  80

Leu Cys Arg Lys Ile Ile Gly Arg Arg Asn Arg Asn Gln Glu Ala Cys
                    85                  90                  95

Lys Ala Val Met
            100

<210> SEQ ID NO 11
<211> LENGTH: 100
<212> TYPE: PRT
<213> ORGANISM: Homo sapiens

<400> SEQUENCE: 11

Met Ala Ser Thr Arg Cys Lys Leu Ala Arg Tyr Leu Glu Asp Leu Glu
 1               5                   10                  15

Asp Val Asp Leu Lys Lys Phe Lys Met His Leu Glu Asp Tyr Pro Pro
                20                  25                  30

Gln Lys Gly Cys Ile Pro Leu Pro Arg Gly Gln Thr Glu Lys Ala Asp
            35                  40                  45

His Val Asp Leu Ala Thr Leu Met Ile Asp Phe Asn Gly Glu Glu Lys
 50                      55                  60

Ala Trp Ala Met Ala Val Trp Ile Phe Ala Ala Ile Asn Arg Arg Asp
 65                  70                  75                  80

Leu Tyr Glu Lys Ala Lys Arg Asp Glu Pro Lys Trp Gly Ser Asp Asn
                    85                  90                  95

Ala Arg Val Ser
            100

<210> SEQ ID NO 12
<211> LENGTH: 100
<212> TYPE: PRT
<213> ORGANISM: Homo sapiens

<400> SEQUENCE: 12

Met Thr Ser Val Arg Cys Lys Leu Ala Gln Tyr Leu Glu Asp Leu Glu
 1               5                   10                  15

Asp Val Asp Leu Lys Lys Phe Lys Met His Leu Glu Asp Tyr Pro Pro
                20                  25                  30

Glu Lys Gly Cys Ile Pro Val Pro Arg Gly Gln Met Glu Lys Ala Asp
            35                  40                  45

His Leu Asp Leu Ala Thr Leu Met Ile Asp Phe Asn Gly Glu Glu Lys
 50                      55                  60

Ala Trp Ala Met Ala Val Trp Ile Phe Ala Ala Ile Asn Arg Arg Asp
 65                  70                  75                  80

Leu Trp Glu Lys Ala Lys Lys Asp Gln Pro Glu Trp Asn Asp Thr Cys
                    85                  90                  95

Thr Ser His Ser
            100

<210> SEQ ID NO 13
<211> LENGTH: 100
<212> TYPE: PRT
<213> ORGANISM: Homo sapiens

```
<400> SEQUENCE: 13

Met Leu Arg Thr Ala Gly Arg Asp Gly Leu Cys Arg Leu Ser Thr Tyr
1               5                   10                  15

Leu Glu Glu Leu Glu Ala Val Glu Leu Lys Lys Phe Lys Leu Tyr Leu
            20                  25                  30

Gly Thr Ala Thr Glu Leu Gly Glu Gly Lys Ile Pro Trp Gly Ser Met
        35                  40                  45

Glu Lys Ala Gly Pro Leu Glu Met Ala Gln Leu Leu Ile Thr His Phe
    50                  55                  60

Gly Pro Glu Glu Ala Trp Arg Leu Ala Leu Ser Thr Phe Glu Arg Ile
65                  70                  75                  80

Asn Arg Lys Asp Leu Trp Glu Arg Gly Gln Arg Glu Asp Leu Val Arg
                85                  90                  95

Asp Thr Pro Pro
            100

<210> SEQ ID NO 14
<211> LENGTH: 100
<212> TYPE: PRT
<213> ORGANISM: Homo sapiens

<400> SEQUENCE: 14

Met Leu Pro Ser Thr Ala Arg Asp Gly Leu Tyr Arg Leu Ser Thr Tyr
1               5                   10                  15

Leu Glu Glu Leu Glu Ala Gly Glu Leu Lys Lys Phe Lys Leu Phe Leu
            20                  25                  30

Gly Ile Ala Glu Asp Leu Ser Gln Asp Lys Ile Pro Trp Gly Arg Met
        35                  40                  45

Glu Lys Ala Gly Pro Leu Glu Met Ala Gln Leu Met Val Ala His Met
    50                  55                  60

Gly Thr Arg Glu Ala Trp Leu Leu Ala Leu Ser Thr Phe Gln Arg Ile
65                  70                  75                  80

His Arg Lys Asp Leu Trp Glu Arg Gly Gln Glu Asp Leu Val Arg
                85                  90                  95

Gly Lys Glu Gly
            100

<210> SEQ ID NO 15
<211> LENGTH: 100
<212> TYPE: PRT
<213> ORGANISM: Homo sapiens

<400> SEQUENCE: 15

Met Gly Arg Ala Arg Asp Ala Ile Leu Asp Ala Leu Glu Asn Leu Thr
1               5                   10                  15

Ala Glu Glu Leu Lys Lys Phe Lys Leu Lys Leu Leu Ser Val Pro Leu
            20                  25                  30

Arg Glu Gly Tyr Gly Arg Ile Pro Arg Gly Ala Leu Leu Ser Met Asp
        35                  40                  45

Ala Leu Asp Leu Thr Asp Lys Leu Val Ser Phe Tyr Leu Glu Thr Tyr
    50                  55                  60

Gly Ala Glu Leu Thr Ala Asn Val Leu Arg Asp Met Gly Leu Gln Glu
65                  70                  75                  80
```

```
Met Ala Gly Gln Leu Gln Ala Thr His Gln Gly Ser Gly Ala Ala
                85                  90                  95

Pro Ala Gly Ile
            100

<210> SEQ ID NO 16
<211> LENGTH: 89
<212> TYPE: PRT
<213> ORGANISM: Homo sapiens
<220> FEATURE:
<221> NAME/KEY: misc_feature
<222> LOCATION: (76)..(76)
<223> OTHER INFORMATION: Xaa can be any naturally occurring amino acid

<400> SEQUENCE: 16

Met Gly Thr Lys Arg Glu Ala Ile Leu Lys Val Leu Glu Asn Leu Thr
1               5                   10                  15

Pro Glu Glu Leu Lys Lys Phe Lys Met Lys Leu Gly Thr Val Pro Leu
                20                  25                  30

Arg Glu Gly Phe Glu Arg Ile Pro Arg Gly Ala Leu Gly Gln Leu Asp
            35                  40                  45

Ile Val Asp Leu Thr Asp Lys Leu Val Ala Ser Tyr Tyr Glu Asp Tyr
50                  55                  60

Ala Ala Glu Leu Val Val Ala Val Leu Arg Asp Xaa Arg Met Leu Glu
65                  70                  75                  80

Glu Ala Ala Arg Leu Gln Arg Ala Ala
                85

<210> SEQ ID NO 17
<211> LENGTH: 100
<212> TYPE: PRT
<213> ORGANISM: Homo sapiens

<400> SEQUENCE: 17

Met Asp Gln Pro Glu Ala Pro Cys Ser Ser Thr Gly Pro Arg Leu Ala
1               5                   10                  15

Val Ala Arg Glu Leu Leu Leu Ala Ala Leu Glu Glu Leu Ser Gln Glu
                20                  25                  30

Gln Leu Lys Arg Phe Arg His Lys Leu Arg Asp Val Gly Pro Asp Gly
            35                  40                  45

Arg Ser Ile Pro Trp Gly Arg Leu Glu Arg Ala Asp Ala Val Asp Leu
50                  55                  60

Ala Glu Gln Leu Ala Gln Phe Tyr Gly Pro Glu Pro Ala Leu Glu Val
65                  70                  75                  80

Ala Arg Lys Thr Leu Lys Arg Ala Asp Ala Arg Asp Val Ala Ala Gln
                85                  90                  95

Leu Gln Glu Arg
            100

<210> SEQ ID NO 18
<211> LENGTH: 100
<212> TYPE: PRT
<213> ORGANISM: Homo sapiens

<400> SEQUENCE: 18

Met Ala Met Ala Lys Ala Arg Lys Pro Arg Glu Ala Leu Leu Trp Ala
1               5                   10                  15

Leu Ser Asp Leu Glu Glu Asn Asp Phe Lys Lys Leu Lys Phe Tyr Leu
                20                  25                  30
```

```
Arg Asp Met Thr Leu Ser Glu Gly Gln Pro Pro Leu Ala Arg Gly Glu
         35                  40                  45

Leu Glu Gly Leu Ile Pro Val Asp Leu Ala Glu Leu Leu Ile Ser Lys
 50                  55                  60

Tyr Gly Glu Lys Glu Ala Val Lys Val Val Leu Lys Gly Leu Lys Val
 65                  70                  75                  80

Met Asn Leu Leu Glu Leu Val Asp Gln Leu Ser His Ile Cys Leu His
                 85                  90                  95

Asp Tyr Arg Glu
            100

<210> SEQ ID NO 19
<211> LENGTH: 100
<212> TYPE: PRT
<213> ORGANISM: Homo sapiens

<400> SEQUENCE: 19

Met Ala Asn Asn Tyr Lys Lys Ile Val Leu Leu Lys Gly Leu Glu Val
 1               5                  10                  15

Ile Asn Asp Tyr His Phe Arg Ile Val Lys Ser Leu Leu Ser Asn Asp
                 20                  25                  30

Leu Lys Leu Asn Pro Lys Met Lys Glu Glu Tyr Asp Lys Ile Gln Ile
             35                  40                  45

Ala Asp Leu Met Glu Glu Lys Phe Pro Gly Asp Ala Gly Leu Gly Lys
 50                  55                  60

Leu Ile Glu Phe Phe Lys Glu Ile Pro Thr Leu Gly Asp Leu Ala Glu
 65                  70                  75                  80

Thr Leu Lys Arg Glu Lys Leu Lys Val Ala Asn Lys Ile Glu Ser Ile
                 85                  90                  95

Pro Val Lys Gly
            100

<210> SEQ ID NO 20
<211> LENGTH: 100
<212> TYPE: PRT
<213> ORGANISM: Homo sapiens

<400> SEQUENCE: 20

Met Gly Lys Lys Tyr Lys Asn Ile Val Leu Leu Lys Gly Leu Glu Val
 1               5                  10                  15

Ile Asn Asp Tyr His Phe Arg Met Val Lys Ser Leu Leu Ser Asn Asp
                 20                  25                  30

Leu Lys Leu Asn Leu Lys Met Arg Glu Glu Tyr Asp Lys Ile Gln Ile
             35                  40                  45

Ala Asp Leu Met Glu Glu Lys Phe Arg Gly Asp Ala Gly Leu Gly Lys
 50                  55                  60

Leu Ile Lys Ile Phe Glu Asp Ile Pro Thr Leu Glu Asp Leu Ala Glu
 65                  70                  75                  80

Thr Leu Lys Lys Glu Lys Leu Lys Val Lys Gly Pro Ala Leu Ser Arg
                 85                  90                  95

Lys Arg Lys Lys
            100

<210> SEQ ID NO 21
<211> LENGTH: 100
<212> TYPE: PRT
<213> ORGANISM: Homo sapiens
```

-continued

<400> SEQUENCE: 21

Met Val Asn Glu Tyr Lys Lys Ile Leu Leu Lys Gly Phe Glu Leu
1               5                   10                  15

Met Asp Asp Tyr His Phe Thr Ser Ile Lys Ser Leu Leu Ala Tyr Asp
            20                  25                  30

Leu Gly Leu Thr Thr Lys Met Gln Glu Glu Tyr Asn Arg Ile Lys Ile
        35                  40                  45

Thr Asp Leu Met Glu Lys Lys Phe Gln Gly Val Ala Cys Leu Asp Lys
50                  55                  60

Leu Ile Glu Leu Ala Lys Asp Met Pro Ser Leu Lys Asn Leu Val Asn
65                  70                  75                  80

Asn Leu Arg Lys Glu Lys Ser Lys Val Ala Lys Lys Ile Lys Thr Gln
                85                  90                  95

Glu Lys Ala Pro
            100

<210> SEQ ID NO 22
<211> LENGTH: 101
<212> TYPE: PRT
<213> ORGANISM: myxoma virus

<400> SEQUENCE: 22

Met Glu His Arg Gly Val Ile Ile Thr Val Leu Glu Asn Leu Ser Asp
1               5                   10                  15

Tyr Gln Phe Lys Met Phe Thr Tyr Leu Ala Met Glu Asp Leu Tyr Ile
            20                  25                  30

Glu Arg Ala Glu Lys Glu Lys Ile Asp Arg Ile Asp Leu Ala His Lys
        35                  40                  45

Ile Ser Glu Gln Tyr Leu Gly Thr Asp Tyr Ile Glu Phe Met Lys Arg
    50                  55                  60

Val Thr Asp Phe Ile Pro Asn Lys Val Tyr Val Asp Ser Leu Leu Ala
65                  70                  75                  80

Arg Ala Glu Ala Asp Ala Glu Ala Thr Met Gly Ala Val Thr Glu Ala
                85                  90                  95

Val Thr Lys Ala Val
            100

<210> SEQ ID NO 23
<211> LENGTH: 101
<212> TYPE: PRT
<213> ORGANISM: shope fibroma virus

<400> SEQUENCE: 23

Met Glu His Arg Gly Val Ile Ile Thr Val Leu Glu Asn Leu Thr Asp
1               5                   10                  15

Tyr Gln Phe Lys Met Phe Leu Tyr Leu Val Thr Glu Asp Leu Arg Ile
            20                  25                  30

Asn Pro Val Glu Lys Glu Lys Ile Asp Arg Ile Asp Leu Ala Tyr Lys
        35                  40                  45

Ile Ser Glu Leu Tyr Pro Gly His Ser Tyr Ile Glu Phe Met Lys Gln
    50                  55                  60

Val Thr Gly Tyr Ile Pro Asn Lys Val Tyr Val Asp Ser Leu Leu Lys
65                  70                  75                  80

```
Asn Ala Glu Glu Asn Thr Gln Asp Leu Phe Asn Thr Pro Lys Lys Gln
                85                  90                  95

Arg Asn Arg Gly Arg
            100

<210> SEQ ID NO 24
<211> LENGTH: 100
<212> TYPE: PRT
<213> ORGANISM: yaba-like disease virus

<400> SEQUENCE: 24

Met Arg Ile Lys Ser Ala Ile Ile Phe Ser Leu Glu Asp Val Thr His
1               5                   10                  15

Tyr Gln Phe Lys Ile Leu Ile Phe Leu Thr Lys Asp Glu Leu Asn Ile
                20                  25                  30

Ser Asp Glu Glu Lys Gln Ile Leu Asp Arg Val Asp Phe Ala Glu Lys
            35                  40                  45

Leu Phe Gln Thr Tyr Pro Gly Ile Lys Ser Leu Tyr Phe Leu Glu Lys
        50                  55                  60

Ala Ile Ser Met Pro Asn Ala Lys Tyr Ala Arg Ser Asn Ile Asn Arg
65                  70                  75                  80

Leu Ile Ser Asp Leu Val Pro Ser Val Gln Phe Glu Pro Val Cys Lys
                85                  90                  95

Lys Ile Ile Arg
            100

<210> SEQ ID NO 25
<211> LENGTH: 100
<212> TYPE: PRT
<213> ORGANISM: swine pox virus

<400> SEQUENCE: 25

Met Glu Leu Arg Thr Tyr Ile Ile Ser Val Leu Glu Arg Leu Thr Pro
1               5                   10                  15

Tyr Gln Phe Lys Thr Leu Leu Phe Leu Ile Gln Asp Asp Ile Asn Ile
                20                  25                  30

Ser Asn Asp Asp Ile Asn Val Leu Asp Arg Val Asp Leu Ala Lys Ile
            35                  40                  45

Met Asn Lys Tyr Asn Asn Tyr Arg Ala Ile Tyr Phe Leu Tyr Lys Val
        50                  55                  60

Ile Leu Arg Ile His Asn Thr Glu Tyr Ile Ser Gly Thr Leu Gln Arg
65                  70                  75                  80

Ser Ile Gln Asn Ile Thr Pro Ile Thr Ser Ser Tyr Thr Tyr Cys Asp
                85                  90                  95

Asn Ser Lys Arg
            100

<210> SEQ ID NO 26
<211> LENGTH: 100
<212> TYPE: PRT
<213> ORGANISM: Homo sapiens

<400> SEQUENCE: 26

Met Ala Lys Thr Pro Ser Asp His Leu Leu Ser Thr Leu Glu Glu Leu
1               5                   10                  15

Val Pro Tyr Asp Phe Glu Lys Phe Lys Phe Lys Leu Gln Asn Thr Ser
                20                  25                  30
```

```
Val Gln Lys Glu His Ser Arg Ile Pro Arg Ser Gln Ile Gln Arg Ala
             35                  40                  45

Arg Pro Val Lys Met Ala Thr Leu Leu Val Thr Tyr Tyr Gly Glu Glu
         50                  55                  60

Tyr Ala Val Gln Leu Thr Leu Gln Val Leu Arg Ala Ile Asn Gln Arg
 65                  70                  75                  80

Leu Leu Ala Glu Glu Leu His Arg Ala Ala Ile Gln Glu Tyr Ser Thr
             85                  90                  95

Gln Glu Asn Gly
            100

<210> SEQ ID NO 27
<211> LENGTH: 100
<212> TYPE: PRT
<213> ORGANISM: Homo sapiens

<400> SEQUENCE: 27

Met Ala Gly Gly Ala Trp Gly Arg Leu Ala Cys Tyr Leu Glu Phe Leu
 1               5                  10                  15

Lys Lys Glu Glu Leu Lys Glu Phe Gln Leu Leu Leu Ala Asn Lys Ala
             20                  25                  30

His Ser Arg Ser Ser Ser Gly Glu Thr Pro Ala Gln Pro Glu Lys Thr
             35                  40                  45

Ser Gly Met Glu Val Ala Ser Tyr Leu Val Ala Gln Tyr Gly Glu Gln
         50                  55                  60

Arg Ala Trp Asp Leu Ala Leu His Thr Trp Glu Gln Met Gly Leu Arg
 65                  70                  75                  80

Ser Leu Cys Ala Gln Ala Gln Glu Gly Ala Gly His Ser Pro Ser Phe
             85                  90                  95

Pro Tyr Ser Pro
            100

<210> SEQ ID NO 28
<211> LENGTH: 37
<212> TYPE: PRT
<213> ORGANISM: Artificial Sequence
<220> FEATURE:
<223> OTHER INFORMATION: Consensus sequence from comparison among POP
      domains

<400> SEQUENCE: 28

Met Arg Leu Met Leu Glu Leu Glu Leu Lys Lys Phe Lys Leu Ile Pro
 1               5                  10                  15

Val Glu Lys Asp Arg Val Glu Leu Ala Leu Leu Val Tyr Ala Ile Leu
             20                  25                  30

Val Phe Met Asp Leu
            35
```